US006803466B1

(12) United States Patent
Lee et al.

(10) Patent No.: US 6,803,466 B1
(45) Date of Patent: Oct. 12, 2004

(54) HIV/FIV PROTEASE INHIBITORS HAVING A SMALL P3 RESIDUE

(75) Inventors: Taekyu Lee, Wilmington, DE (US); Chi-Huey Wong, Rancho Santa Fe, CA (US); John H. Elder, Rancho Santa Fe, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/581,044

(22) PCT Filed: Dec. 8, 1998

(86) PCT No.: PCT/US98/25964

§ 371 (c)(1), (2), (4) Date: Jun. 8, 2000

(87) PCT Pub. No.: WO99/29311

PCT Pub. Date: Jun. 17, 1999

Related U.S. Application Data

(60) Provisional application No. 60/067,959, filed on Dec. 8, 1997.

(51) Int. Cl.[7] ...................... A61K 31/165; A61K 31/38; A61K 31/405; A61K 31/47; A61K 38/05

(52) U.S. Cl. ........................... 546/146; 514/18; 514/19; 514/307; 514/423; 530/330; 530/331; 548/204; 548/537; 564/381

(58) Field of Search ................................ 564/374, 381, 564/503, 507; 560/21, 22, 156; 548/204, 537; 546/146; 530/330, 331; 514/18, 19, 307, 365, 423, 483, 487, 488, 489, 654, 667, 669

(56) References Cited

U.S. PATENT DOCUMENTS

| | | | | |
|---|---|---|---|---|
| 5,157,041 A | * | 10/1992 | Handa et al. | 514/314 |
| 5,294,720 A | * | 3/1994 | Jadhav et al. | 546/265 |
| 5,354,866 A | * | 10/1994 | Kempf et al. | 546/265 |
| 5,502,060 A | * | 3/1996 | Thompson et al. | 514/307 |
| 5,541,321 A | * | 7/1996 | Baker et al. | 546/14 |
| 5,552,405 A | * | 9/1996 | Gorys et al. | 514/267 |
| 5,567,823 A | * | 10/1996 | Tien et al. | 548/204 |
| 5,733,906 A | * | 3/1998 | Jungheim et al. | 514/222.2 |

FOREIGN PATENT DOCUMENTS

| | | | |
|---|---|---|---|
| EP | 751145 | * | 1/1997 |
| WO | 92/00948 | * | 1/1992 |
| WO | 93/23361 | * | 11/1993 |
| WO | 97/21100 | * | 6/1997 |

OTHER PUBLICATIONS

Dreyer et al. A Symmetric Inhibitor Binds HIV–1 Protease In Biochemistry. vol. 32, No. 3, pp. 937–947, 1993.*

Tam et al. Intriguing Structure–Activity Relations Underlie J. Med. Chem. vol. 35, No. 7, pp. 1318–1320, 1992.*

Huff, "HIV Protease: A Novel Chemotherapeutic Target for AIDS",*J. Med. Chem. 34*: 2305–2314 (1991).

(List continued on next page.)

*Primary Examiner*—Jeffrey Edwin Russel
(74) *Attorney, Agent, or Firm*—Donald G. Lewis

(57) ABSTRACT

With the help of X-ray structural analyses of drug-resistant HIV proteases and molecular modeling, a new type of inhibitor with a small P3 residue has been developed. These inhibitors are effective against HIV and its drug-resistant mutants, as well as FIV. Modification of existing HIV protease inhibitors effective against the wild type and drug-resistant mutants and further supports that FIV protease is a useful model for drug-resistant HIV proteases, which often are developed through reduction in size of the binging region for the P3 group or the combined P3 and P1 groups.

13 Claims, 16 Drawing Sheets

1000a X = Cbz
1200 X = Cbz-Ala

2a X = Cbz
2b X = Cbz-Ala-Val

3a X = Cbz
3b X = Cbz-Ala-Val

4a X = Cbz
4b X = Cbz-Ala-Val

5a X = Cbz
5b X = Cbz-Ala-Val

6a X = H
6b X = Cbz-Ala-Val

7 X = BOC
7a X = Cbz-Ala-Val
7b X = Cbz-Ala-Asn

RO31-8959

ABT-538

OTHER PUBLICATIONS

Otto, et al., "In vitro isolation and identification of human immunodeficiency virus (HIV) variants with reduced sensitivity to C–2 Symmetrical inhibitors of HIV type 1 protease", *Proc. Natl. Acad. Sci. USA 90*: 7543–7547 m(1993).

Wlodawer, et al., "Structure–Based Inhibitors of HIV–1 Protease", *Annu. Rev. Biochem. 62*: 543–585 (1993).

Condra, et al., "In vivo emergence of HIV–1 variants resistant to multiple protease inhibitors", *Nature 374*: 569–571 (1995).

Wlodawer, et al., "Structure of an inhibitor complex of the proteinase from feline immunodeficiency virus", *Nature Struct. Biol. 2*: 480–488 (1995).

Erickson, "The not–so–great escape", *Nature Struct. Biol. 2*: 523–529 (1995).

Slee, et al., "Selectivity in the Inhibition of HIV and FIV Protease: Inhibitory and Mechanistic Studies of Pyrrolidine–Containing α–Keto Amide and Hydroxyethylamine Core Structures", *J. Am. Chem. Soc. 117*: 11867–11878 (1995).

Budt, et al., "HIV Protease Inhibitor HOE/BAY 793, Structure–Activity Relationships in a Series of $C_2$–Symmetric Diols", *Bioorg. Med. Chem. 3*: 559–571 (1995).

Gulnik, et al., "Kinetic Characterization and Cross–Resistance Patterns of HIV–1 Protease Mutants Selected under Drug Pressure", *Biochemistry 34*: 9282–9287 (1995).

Erickson, et al., "Structural Mechanisms of HIV Drug Resistance", *Annu. Rev. Pharmacol. Toxicol. 36*: 545–571 (1996).

De Lucca, et al., "Cyclic HIV Protease Inhibitors capable of displacing the active site structural waster molecule" *Drug Discovery Today 2*: 6–18 (1997).

Wilson, et al., "Escape Mutants of HIV–1 Proteinase: Enzymic Efficiency and Susceptibility to Inhibition", *Biochim. Biophys. Acta 1339*: 113–115 (1997).

Vacca, et al., "Clinically Effective HIV–1 Protease Inhibitors", *Drug Discovery Today 2*: 261–272 (1997).

Wong, et al., "Recovery of Replication–Competent HIV Despite Prolonged Suppression of Plasma Viremia", *Science 278*: 1291–1295 (1997).

Finzi, et al., "Identification of a Reservoir of HIV–1 in Patients on Highly Active Antiretroviral Therapy", *Science 278*: 1295–1300 (1997).

Lee, et al., "Analysis of the S3 and S3' subsite specificities of feline immunodeficiency virus (FIV) protease: Development of a broad–based protease inhibitor efficacious against FIV, SIV, and HIV in vitro and ex vivo", *Proc. Natl. Acad. Sci. USA 95*: 939–944 (1998).

* cited by examiner

1b

A-76889

1000a X = Cbz
1200 X = Cbz-Ala

2a X = Cbz
2b X = Cbz-Ala-Val

3a X = Cbz
3b X = Cbz-Ala-Val

4a X = Cbz
4b X = Cbz-Ala-Val

5a X = Cbz
5b X = Cbz-Ala-Val

6a X = H
6b X = Cbz-Ala-Val

7 X = BOC
7a X = Cbz-Ala-Val
7b X = Cbz-Ala-Asn

RO31-8959

ABT-538

14

15 R = Cbz
16 R = H

17 R = Cbz
18 R = H

19 X = Ala-Cbz
20 X = Leu-Cbz
21 X = Phe-Cbz
22 X = Val-Cbz

8 X = Ala-Cbz
9 X = Leu-Cbz
10 X = Phe-Cbz
11 X = Val-Cbz

23

12 X = Ser-Cbz
13 X = Thr-Cbz 24
25
2a X = H
2b X = Cbz-Ala-Val

26

24

3a and 3b X = H, Y = O

5a X, Y = O 4a and 4b X = H, Y = O

5b X, Y = O 27 28 29 6a 6b 31

| compd | FIV PR[b] $K_i$ (nM) | HIV PR[c] $K_i$ (nM) | $IC_{50}$ (nM) | HIV (G48V)[c] $IC_{50}$ (nM) | HIV (V82F)[c] $IC_{50}$ (nM) |
|---|---|---|---|---|---|
| **1000a** | 17000 ± 300[d] | 1.1 ± 0.2[d] | | | |
| **1200** | 41 ± 7[d] | 1.5 ± 0.3[d] | 3.8 | 20.5 | 14.9 |
| **2a** | NI | | 60000[e] | | |
| **2b** | 7300 ± 300 | 499 ± 81 | | | |
| **3a** | NI | | 300000[e] | | |
| **3b** | 9400 ± 900 | 308 ± 70 | | | |
| **4a** | NI | | 2000[e] | | |
| **4b** | 212 ± 23 | 5.4 ± 0.7 | 10.3 | 131.0 | 86.1 |
| **5a** | NI | 214[e] | | | |
| **5b** | 46 ± 5 | 2.5 ± 0.4 | 7.8 | 68.7 | 44.4 |
| **6** | 3700 ± 600 | 3.0 ± 0.6 | 5.0 | 34.5 | 24.0 |
| **7a** | 2600 ± 300 | 1.5 ± 0.2 | 4.0 | 26.1 | 13.3 |
| **7b** | 133000 ± 38000 | 11.3 ± 1.3 | | | |
| **RO31-8959** | 76000± 300[b] | 1.6 ± 0.6[c] 0.0003[f] | | 0.0081[f] | 0.0005[f] |
| **ABT-538** | | 0.0001[f] | | 0.0017[f] | 0.009[f] |

FIG. 10

| Inhibitor (X) | FIV PR[b] $K_i$(nM) | HIV PR[c] $K_i$(nM) | Inhibitor (Y) | FIV PR[b] $K_i$(nM) | HIV PR[c] $K_i$(nM) |
|---|---|---|---|---|---|
| **8** (Ala-Cbz) | 62 ± 9 | 6.5 ± 1.3 | **1b** (Ala-Cbz) | 41 ± 7[d] | 1.5 ± 0.3[d] |
| **9** (Leu-Cbz) | 230 ± 34 | 0.87 ± 0.12 | **9b** (Leu-Cbz) | 159 ± 15[d] | 1.4 ± 0.3[d] |
| **10** (Phe-Cbz) | 487 ± 20 | 5.5 ± 0.8 | **10b** (Phe-Cbz) | 7,000 ± 500[d] | 2.6 ± 0.4[d] |
| **11** (Val-Cbz) | 248 ± 47 | nd | **12** (Ser-Cbz) | 32 ± 5 | 0.58 ± 0.1 |
| | | | **13** (Thr-Cbz) | 142 ± 25 | 7.7 ± 1.9 |

100

200 R=Cbz
300 R=H

400 R=Cbz
500 R=H

600 X=Gly-Cbz
700 X=Ala-Cbz
800 X=Leu-Cbz
900 X=Phe-Cbz

400

1000 X=Cbz
1100 X=Gly-Cbz
1200 X=Ala-Cbz
1300 X=Leu-Cbz
1400 X=Phe-Cbz (i) 2,2-dimethoxypropane, *p*-TsOH, 80%; (ii) Pd/C, $H_2$, MeOH, 99%; (iii) HBTU, Cbz-Val, $Et_3N$, $CH_3CN$, 89%; (iv) HBTU, Cbz-amino acids, $Et_3N$, $CH_3CN$; (v) *p*-TsOH, MeOH.

R03189

$K_i$=0.7 nM for HIV[7]

$K_i$=67 μM for FIV

DMP323

$K_i$=0.3 nM for HIV[8]

$IC_{50}$=7.3 mM for FIV

HOE/BAY793

$IC_{50}$=0.3 nM for HIV[9]

$IC_{50}$=20 μM for FIV

• R=*t*-Bu $K_i$=0.2 μM for HIV[10]

$IC_{50}$>7 mM for FIV[10]

• R=Ile-Gln-O-*t*-Bu $K_i$=0.15 μM for HIV[10]

$IC_{50}$=25 μM for FIV[10]

SEQUENCE LISTING

```
<160> NUMBER OF SEQ ID NOS: 9

<210> SEQ ID NO 1
<211> LENGTH: 8
<212> TYPE: PRT
<213> ORGANISM: Artificial Sequence
<220> FEATURE:
<223> OTHER INFORMATION: synthesized
<221> NAME/KEY: ACETYLATION
<222> LOCATION: (1)...(1)

<400> SEQUENCE: 1

Pro Gln Ala Tyr Pro Ile Gln Thr
 1               5


<210> SEQ ID NO 2
<211> LENGTH: 6
<212> TYPE: PRT
<213> ORGANISM: Artificial Sequence
<220> FEATURE:
<223> OTHER INFORMATION: synthesized
<221> NAME/KEY: ACETYLATION
<222> LOCATION: (1)...(1)

<400> SEQUENCE: 2

Gln Ala Tyr Pro Ile Gln
 1               5


<210> SEQ ID NO 3
<211> LENGTH: 6
<212> TYPE: PRT
<213> ORGANISM: Artificial Sequence
<220> FEATURE:
<223> OTHER INFORMATION: synthesized
<221> NAME/KEY: MOD_RES
<222> LOCATION: (1)...(1)
<223> OTHER INFORMATION: Abz
<221> NAME/KEY: VARIANT
<222> LOCATION: (3)...(3)
<223> OTHER INFORMATION: Xaa is norleucine
<221> NAME/KEY: MOD_RES
<222> LOCATION: (4)...(4)
<223> OTHER INFORMATION: p-NO2
<221> NAME/KEY: AMIDATION
<222> LOCATION: (6)...(6)

<400> SEQUENCE: 3

Thr Ile Xaa Phe Gln Arg
 1               5


<210> SEQ ID NO 4
<211> LENGTH: 17
<212> TYPE: PRT
<213> ORGANISM: Artificial Sequence
```

-continued

<220> FEATURE:
<223> OTHER INFORMATION: synthesized

<400> SEQUENCE: 4

Gly Lys Glu Glu Gly Pro Pro Gln Ala Tyr Pro Ile Gln Thr Val Asn
 1               5                  10                  15

Gly

<210> SEQ ID NO 5
<211> LENGTH: 14
<212> TYPE: PRT
<213> ORGANISM: Artificial Sequence
<220> FEATURE:
<223> OTHER INFORMATION: synthesized
<221> NAME/KEY: MOD_RES
<222> LOCATION: (5)...(5)
<223> OTHER INFORMATION: Abz

<400> SEQUENCE: 5

Arg Ala Leu Thr Lys Val Gln Phe Val Gln Ser Lys Gly Arg
 1               5                  10

<210> SEQ ID NO 6
<211> LENGTH: 45
<212> TYPE: DNA
<213> ORGANISM: Artificial Sequence
<220> FEATURE:
<223> OTHER INFORMATION: synthesized

<400> SEQUENCE: 6
atctctcccc aataatggta ctattaatga gttatcttct aagac 45

<210> SEQ ID NO 7
<211> LENGTH: 41
<212> TYPE: DNA
<213> ORGANISM: Artificial Sequence
<220> FEATURE:
<223> OTHER INFORMATION: synthesized

<400> SEQUENCE: 7
actattggac atatggcata taataaagta ggtactacta c 41

<210> SEQ ID NO 8
<211> LENGTH: 39
<212> TYPE: DNA
<213> ORGANISM: Artificial Sequence
<220> FEATURE:
<223> OTHER INFORMATION: synthesized

<400> SEQUENCE: 8
atcagaaagc ttttacatta ctaacctgat attaaattt 39

<210> SEQ ID NO 9
<211> LENGTH: 45
<212> TYPE: DNA
<213> ORGANISM: Artificial Sequence
<220> FEATURE:
<223> OTHER INFORMATION: synthesized

<400> SEQUENCE: 9
ggaaggcaaa atatgattgg aattggagga ggaaagagag gaaca 45

HIV/FIV PROTEASE INHIBITORS HAVING A SMALL P3 RESIDUE

CROSS-REFERENCE TO RELATED APPLICATION

The present application claims priority from and is a national stage application under 35 U.S.C. §371 of copending International Application No. PCT/US98/25964, filed Dec. 8, 1998 and published in English, which claims priority, under 35 U.S.C. §119(e), from provisional application Serial No. 60/067,959, filed Dec. 8, 1997, the disclosure of which are hereby incorporated by reference.

FIELD OF THE INVENTION

The invention relates to HIV and FIV protease inhibitors. More particularly, the invention is directed to HIV and FIV protease inhibitors characterized by core structures having a small P3 residue. The invention is also directed to methods for making such compounds with clinically useful activity and which are potentially resistive against loss of inhibitory activity due to development of resistant strains of HIV.

BACKGROUND

The aspartyl protease (PR) of human immunodeficiency virus (HIV) has been the subject of extensive research for the development of therapeutically useful inhibitors to control the progression of human acquired immunodeficiency syndrome (AIDS). Four competitive inhibitors of this enzyme have been approved and several others are in clinical trials (Babine et al. Chem. Rev. 1997, 97, 1359–1472; De Lucca et al. Drug Discovery Today 1997, 2, 6–18; Vacca et al. Drug Discovery Today 1997, 2, 261–272; Huff et al. J. Med. Chem. 1991, 34, 2305; Wlodawer et al. Ann. Rev. Biochem. 1993, 62, 543–585). Despite the high potency and high selectivity of these inhibitors used in AIDS therapy, many drug-resistant variants of HIV have been identified, including 45 distinct drug-resistant variants found in the past 3 years.

The drug-resistant mutants are generated through incomplete suppression of the virus by inhibitors clinically and usually contain multiple substitutions in their proteases. Moreover, these mutant enzymes often exhibit cross-resistance to many structurally distinct protease inhibitors. Therefore, development of new broad-based protease inhibitors efficacious against a wide spectrum of HIV variants may be necessary in order to slow down the development of drug resistance (Schinazi et al. Int. Antiviral News 1997, 5, 129–142; Wilson et al. J. Biochim. Biophy. Acta 1997, 1339, 113–125; Erickson et al. Annu. Rev. Pharmacol. Toxicol. 1996, 36, 545–571; Gulnik et al. Biochemistry 1995, 34, 9282–9287; Erickson et al. Nature Struct. Biol. 1995, 2, 523–529; Condra et al. Nature, 1995, 374, 569–571; Otto et al. Proc. Natl. Acad. Sci. USA 1993, 90, 7543–7547; Wong et al. Science, 1997, 278, 1291–1295; Finzi et al. Science, 1997, 278, 1295–1300).

FIV is a retrovirus which causes an immunodeficiency syndrome in cats comparable to AIDS in humans (Talbott et al. Proc. Natl. Acad. Sci. USA 1989, 86, 5743–5747; Pedersen et al. Science 1987, 235, 790–793). Both HIV and FIV PRs are C2-symmetric homodimeric enzymes, and they have almost superimposable active-site structures that facilitate catalysis by an identical mechanism (Slee et al. J. Am. Chem. Soc. 1995, 117, 11867–11878). Similar to HIV PR, FIV PR also processes both structural proteins of gag and the enzymes encoded by pol during FIV replication (Kramer et al. Science 1986, 231, 1580–1584) Furthermore, six mutated residues in HIV PR causing drug resistance (K20I, V32I, I50V, N88D, L90M, Q92K; Mellors et al. Int. Antiviral News, 1995, 3, 8–13) are found in the structurally aligned native residues of FIV PR.

Kinetic studies have also demonstrated that various potent HIV PR inhibitors which interact with the binding region from S4 to S4' are less efficient inhibitors of FIV PR by a factor of 100 or more and good inhibitiors of FIV PR are often better inhibitors of the wild-type and drug-resistant HIV PRs. In addition to the observation that FIV PR resembles many known drug-resistant HIV PRs, the cat offers a potential animal system to test the effectiveness of anti-lentiviral agents in vivo to speed up the drug development process.

What is needed are combinatorial libraries of HIV and FIV protease inhibitors and simple synthetic methods for making same.

Furthermore, what is needed is a class of HIV and FIV protease inhibitors having enhanced possibilities of variability at the binding region for improving binding between the enzyme and its inhibitor.

Finally, what is needed are new HIV and FIV protease inhibitors having clinically useful inhibitory activity and a resistivity to a loss of inhibitory activity due to development of resistant strains of HIV.

BRIEF SUMMARY OF THE INVENTION

One aspect of the invention is directed to a protease inhibitor represented by the following structure:

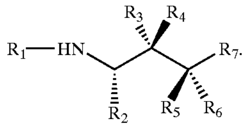

In the above structure, $R_1$ may be any of the following radicals: hydrogen, carbobenzyloxy-, carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-alanine-asparagine-, carbobenzyloxy-threonine-valine- and carbobenzyloxy-valine-valine-. $R_2$ may be any of the following radicals: $—CH_2$-Phenyl, and $—CH_2—CH(CH_3)_2$. $R_3$ may be any of the following radicals: hydrogen, oxygen and hydroxyl; $R_4$ is selected from the group consisting of hydrogen, oxygen and hydroxyl, wherein $R_3$ and $R_4$ are not both hydroxyl and wherein $R_3$ and $R_4$ are either a single combined oxygen forming a carbonyl group. $R_5$ may be any of the following radicals: hydrogen, and oxygen; $R_6$ is selected from the group consisting of hydrogen, and oxygen, wherein $R_5$ and $R_6$ are either a single combined oxygen forming a carbonyl group or both seperately hydrogen. $R_7$ is a radical represented by the formula:

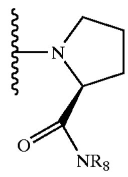

wherein $R_8$ is a radical selected from the group consisting of —$(H)_2$, and —H(t-Butyl).

Another aspect of the invention is directed to a protease inhibitor represented by the following structure:

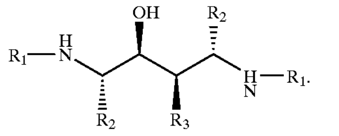

In the above structure, $R_1$ may be any of the following radicals: hydrogen, carbobenzyloxy-, carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine-, carbobenzyloxy-alanine-asparagine- and carbobenzyloxy-valine-valine-. $R_2$ may be any of the following radicals: —$CH_2$-Phenyl, and —$CH_2$—$CH(CH_3)_2$. $R_3$ is either hydrogen or —OH.

Another aspect of the invention is directed to a protease inhibitor represented by the following structure:

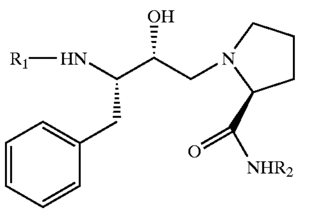

In the above structure, $R_1$ may be any of the following radicals: hydrogen, carbobenzyloxy-, carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine- , carbobenzyloxy-alanine-asparagine- and carbobenzyloxy-valine-valine-. $R_2$ is either —$(H)_2$ or —H(t-Butyl).

Another aspect of the invention is directed to a protease inhibitor represented by the following structure:

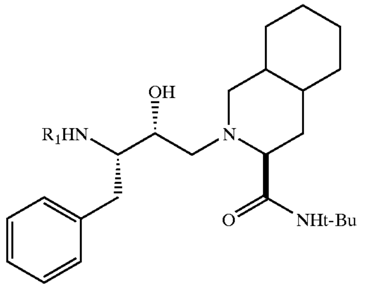

In the above structure, $R_1$ may be any of the following radicals: hydrogen, carbobenzyloxy-, carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine-, carbobenzyloxy-valine-valine- and carbobenzyloxy-alanine-asparagine-.

Another aspect of the invention is directed to protease inhibitor represented by the following structure:

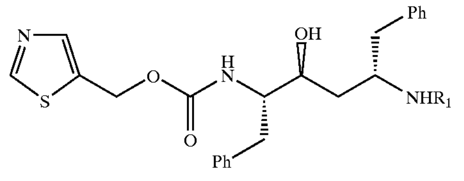

In the above structure, $R_1$ may be any of the following radicals: hydrogen, carbobenzyloxy-, carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine-, carbobenzyloxy-valine-valine- and carbobenzyloxy-alanine-asparagine-.

DESCRIPTION OF FIGURES

FIG. 10 tabulates the inhibition of FIV and HIV PRs by small P3 residue containing inhibitors and their parent compounds wherein the superscript are each described as follows: Ki and IC50 values were determined in duplicate using fluorescent substrate (For procedures see Lee et al. Proc. Natl. Acad. Sci. USA 1998, 95, 939–944; for HIV PR substrate, see Toth, M. V.; Marshall, G. R. *Int. J. Peptide Res.* 1990, 36, 544); b) Data obtained at pH 5.25 at 370 C in 0.1M $NaH_2PO_4$, 0.1 M sodium citrate, 0.2 M NaCl, 0.1 mM DTT, 5% glycerol, and 5% DMSO in volume; c) Data obtained at pH 5.25 at 370 C in 0.1 M MES, 5% glycerol, and 5% DMSO in volume; d) From Lee et al. Proc. Natl. Acad. Sci. USA 1998, 95, 939–944; e) From Slee et al. J. Am. Chem. Soc. 1995, 117, 11867–11878; f) From Wilson et al. J. Biochim. Biophy. Acta 1997, 1339, 113–125; NI, No inhibition at 800 $\mu$M of inhibitor.

DETAILED DESCRIPTION OF THE INVENTION

Figure 1A:
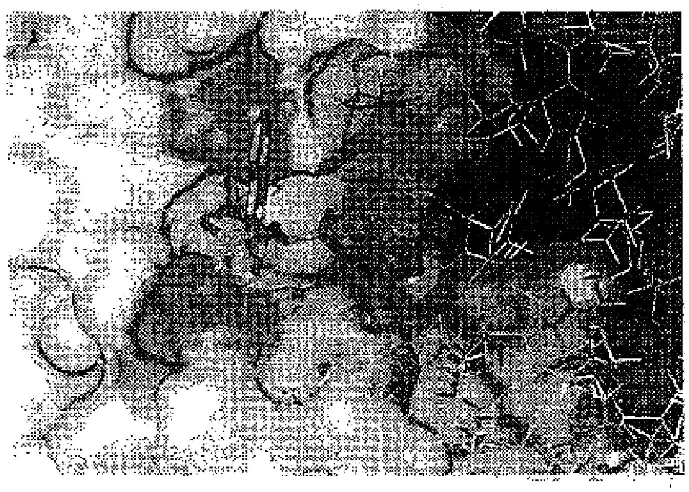
FIG. 1 illustrates models of HIV protease (top) and FIV protease (middle) complexed with 1b. The models show the small S3 site in FIV protease and the close proximity of the P3 (CH3) and P1 (PhCH2) residues, a structural feature found in many drug-resistant HIV proteases. Bottom: shown is a cut-away view of the molecular surfaces of HIV (pink) and FIV PR (blue), in which the dipping plane is parallel to the plane of the two aspartates and cuts inside the P3 site.

The invention is directed to potent inhibitors against human immunodeficiency virus protease (HIV PR) and feline immunodeficiency virus protease (FIV PR), which has been shown to be a useful model for drug-resistant mutant HIV PRs (Slee et al. J. Am. Chem. Soc. 1995, 117, 11867–11878; Lee et al. Proc. Natl. Acad. Sci. USA 1998, 95, 939–944). It is disclosed herein that FIV PR provides a good model of drug resistance in retroviral proteases. Testing candidate drugs with respect to their inhibitory activity against both HIV and FIV proteases and determining which inhibitors are simultaneously efficacious against both of these mechanistically identical proteases, identifies inhibitors of HIV protease which are potentially less prone to resistance development. Candidate drugs which are successfully screened in vitro may then be tested in cats as model systems on which to test HIV PR inhibitors in vivo.

More particularly, the invention is directed to a new type of inhibitor with a small P3 residue. These inhibitors are effective against HIV and its drug-resistant mutants, as well as FIV. Modification of existing HIV protease inhibitors by reducing the size of the P3 residue has the same effect. This finding provides a new strategy for the development of HIV protease inhibitors effective against the wild type and drug-resistant mutants and further supports that FIV protease is a useful model for drug-resistant HIV proteases, which often are developed through reduction in size of the binding region for P3 group or the combined P3 and P1 groups.

EXAMPLE 1

Redesign of C2-Symmetric Inhibitors with Small P3 Residues

Our initial work on the development of protease inhibitors efficacious against both HIV and FIV was focused on the systematic analysis of the S3 and S3' subsite specificities of the enzymes using a series of C2-symmetric inhibitors containing (1S,2R,3R,4S)-1,4-diamino-1,4-dibenzyl-2,3-butandiol as a P1 and P1' core and Val as P2 and P2' residues (Lee et al. Proc. Natl. Acad. Sci. USA 1998, 95, 939–944). We have demonstrated that FIV PR exhibited a strong preference for small hydrophobic groups at the S3 and S3' subsites in contrast to the high flexibility for the P3 and P3' residues binding to HIV PR (ibid, 939–944). Kinetic studies have also indicated that the binding preference observed in drug-resistant mutant HIV PRs is very similar to that found in FIV PR (ibid, 939–944) In addition, the most potent FIV PR inhibitor 1b (FIG. 3) strongly inhibits FIV, HIV, and SIV infections in tissue culture with virtually the same degree of effectiveness.

The x-ray structure of FIV PR complexed with inhibitor 1b has been determined and shown that the P1 and P3 side chains are positioned very closely, consistent with previous structural studies for HIV and FIV PRs that S1 and S3 subsites are neighboring hydrophobic pockets to accommodate the corresponding P1 and P3 side chains (The x-ray structure of 1b complexed with HIV, FIV (3X), FIV (V59I), and FIV (Q99V) PRs have been determined and will be published separately: Li et al. Biochemistry, unpublished as of filing). Models of 1b bound to HIV and FIV PR (FIG. 1) indicate that the S1 and S3 subsites in HIV PR constitute a much larger hydrophobic pocket than the corresponding subsites found in FIV PR. Because of this smaller hydrophobic size, FIV PR can only accommodate inhibitors with a smaller size for P1 and P3 residues together, and several drug-resistant HIV PRs are indeed found to have a smaller domain composed of S3 and S1 subsites.

Figure 1B:
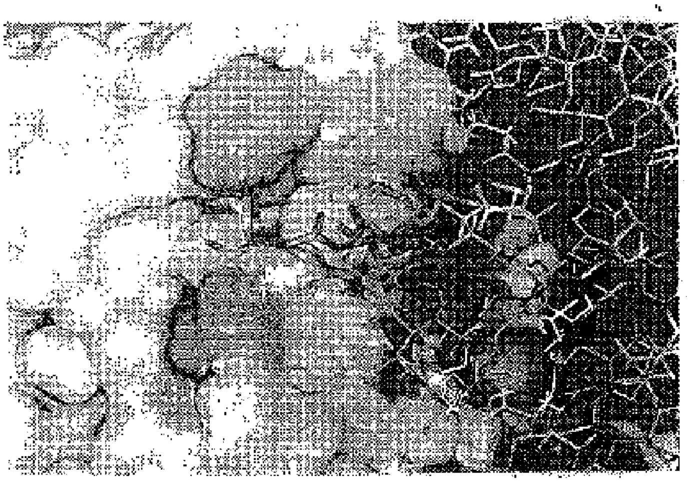
Figure 1C:
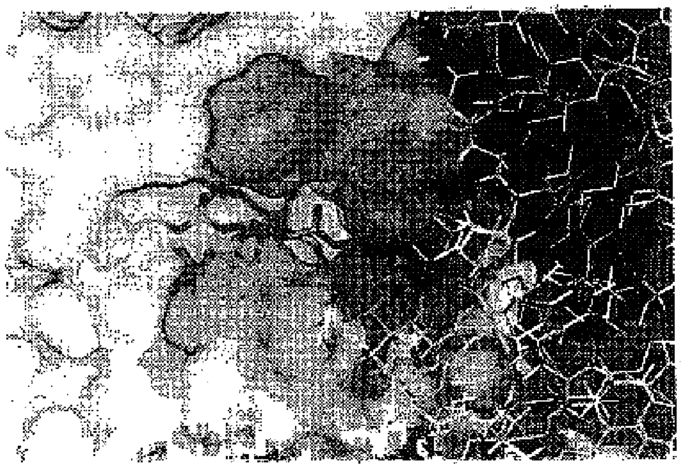
Figure 2:
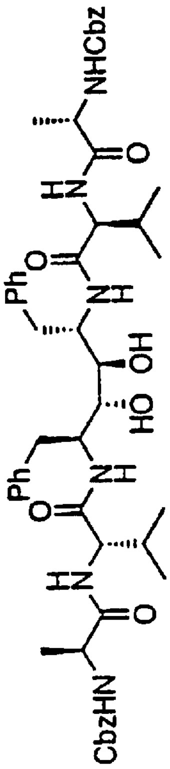
FIG. 2 shows the amino acid side chains in the S subsites interacting with the inhibitors are indicated.
Figure 2:
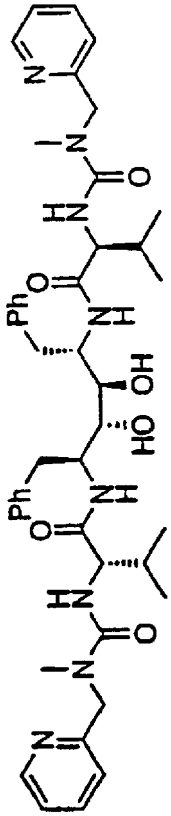
Figure 2:
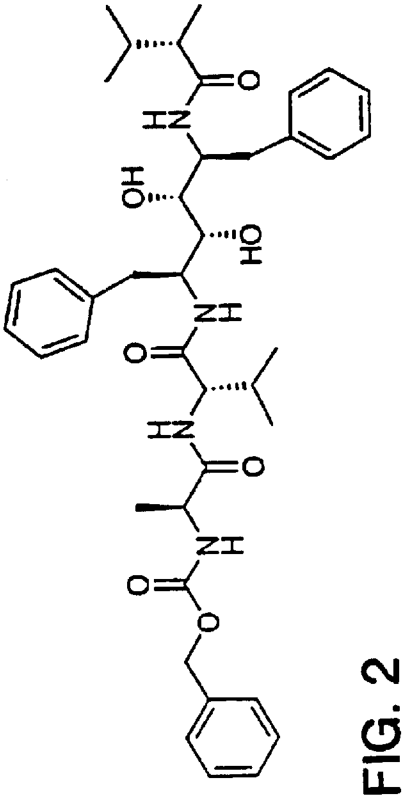
Figure 2:
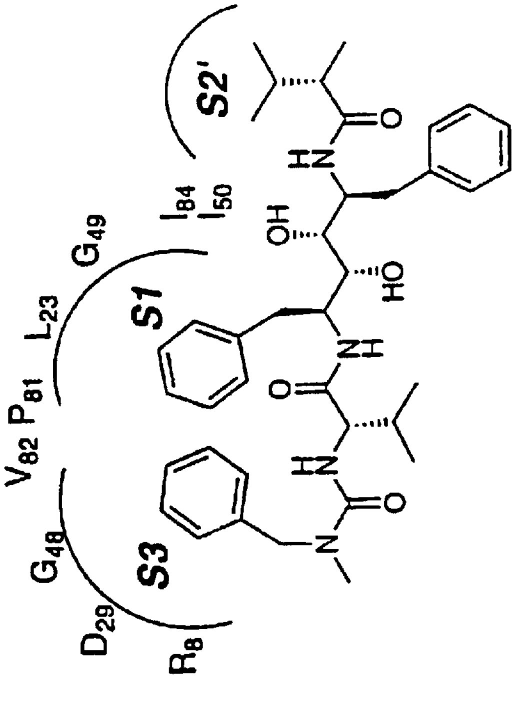

Based on the x-ray structures of HIV and FIV PRs complexed with inhibitors, the residues which define the S subsites are shown in FIG. 2. In HIV PR, Pro 81 and Val 82 are components for both S1 and S3 subsites since they can affect binding of both P1 and P3 moieties, whereas Ile 98 and Gln 99 are the structurally aligned residues for FIV PR (Hosur et al. J. Am. Chem. Soc. 1994, 116, 847–855). The x-ray structures also revealed that three residues at S3 and S3' subsites, Gly 48, Pro 81, and Val 82 of HIV PR, were replaced with Ile 57, Ile 98, and Gln 99 in FIV PR. As a result, the S3 and S3' subsites of FIV PR are sterically more congested than those in HIV PR, and these three different residues may define the S3 and S3' subsite specificities of the enzymes. The results of these studies point to a new direction for development of inhibitors effective against both HIV PR and its drug-resistant variants as shown in FIGS. 1 and 2.

EXAMPLE 2

Dissymmetric Inhibitors with Small P3 Groups

Figure 3:
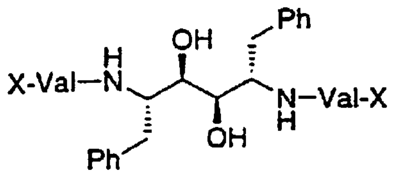
FIG. 3 illustrates the dissymmetric inhibitors with small P3residues. Compounds 2b–6b and 7 contain a methyl group as P3 residue.
Figure 3:
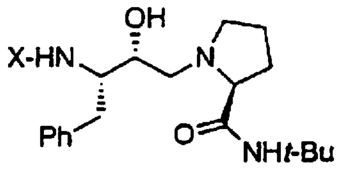
Figure 3:
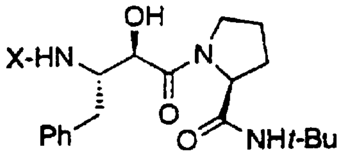
Figure 3:
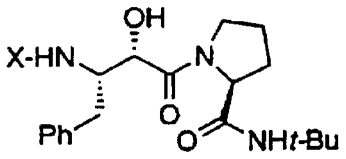
Figure 3:
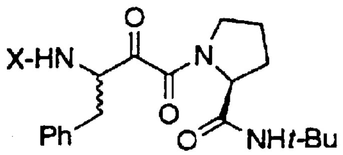
Figure 3:
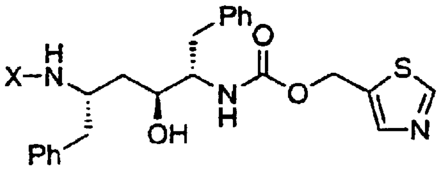
Figure 3:
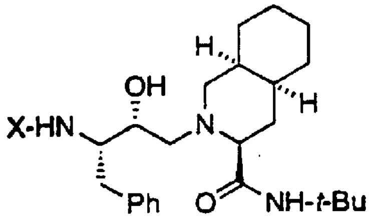
Figure 3:
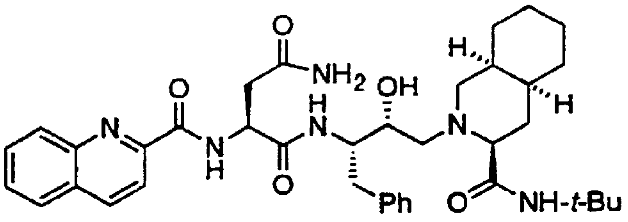
Figure 3:
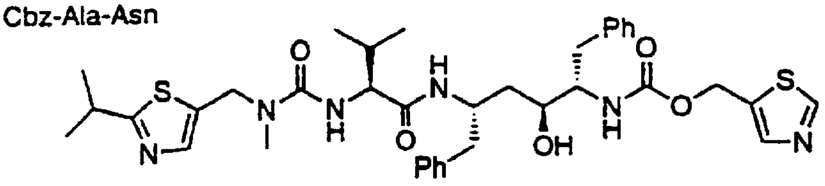

The S3 and S3' subsite specificities of FIV PR and drug-resistant HIV PRs with mutations affecting the S3 subsite were investigated further to determine if there is a correlation between them. The new inhibitors of HIV PR were synthesized with Ala at P3, Val or Asn at P2, and various Phe-Pro isosteric cores for the P1-P1' residues (FIG. 3). The inhibitory activities of each compound against FIV, HIV, and drug-resistant mutant HIV PRs were determined as described previously (Lee et al. Proc. Natl. Acad. Sci. USA 1998, 95, 939–944) and the results are summarized in FIG. 10.

Each compound tested in this study is a competitive inhibitor and is significantly more potent against HIV PR than FIV PR, as expected. However, the new inhibitors 1b–6b, and 7a showed a remarkable different pattern of inhibitory activities compared to their parent compounds 1a–5a, ABT-538 and R031-8959. Compounds 2a–4a, containing no P3 moieties, exhibited marginal activities with $IC_{50}$ value in the range of 2–300 $\mu$M against HIV PR and did not show any significant inhibition of FIV PR at 800 $\mu$M. Only the $\alpha$-keto amide 5a showed reasonable potency against HIV PR with a $K_i$ value of 214 nM (Slee et al. J. Am. Chem. Soc. 1995, 117, 11867–11878). On the other hand, the modified inhibitors 2b–5b, which contain a methyl group as P3 residue, displayed 120- to 1000-fold improved inhibitory activities against HIV PR and at least three orders of magnitude higher potency for FIV PR compared to their parent compounds. In particular, 5b was found to be a slow binding inhibitor with $K_i$of 2.5 and 46 nM against HIV and FIV PR, respectively. This level of potency against FIV PR by the inhibitor with a molecular weight of only 649 was truly remarkable, considering the smallest efficient substate for the enzyme is an eight-residue peptide, Ac-Pro-Gln-Ala-Tyr~Pro-Ile-Gln-Thr (SEQ ID NO: 1) (Schnlzer et al. Virology 1996, 224, 268–275).

Figure 4:
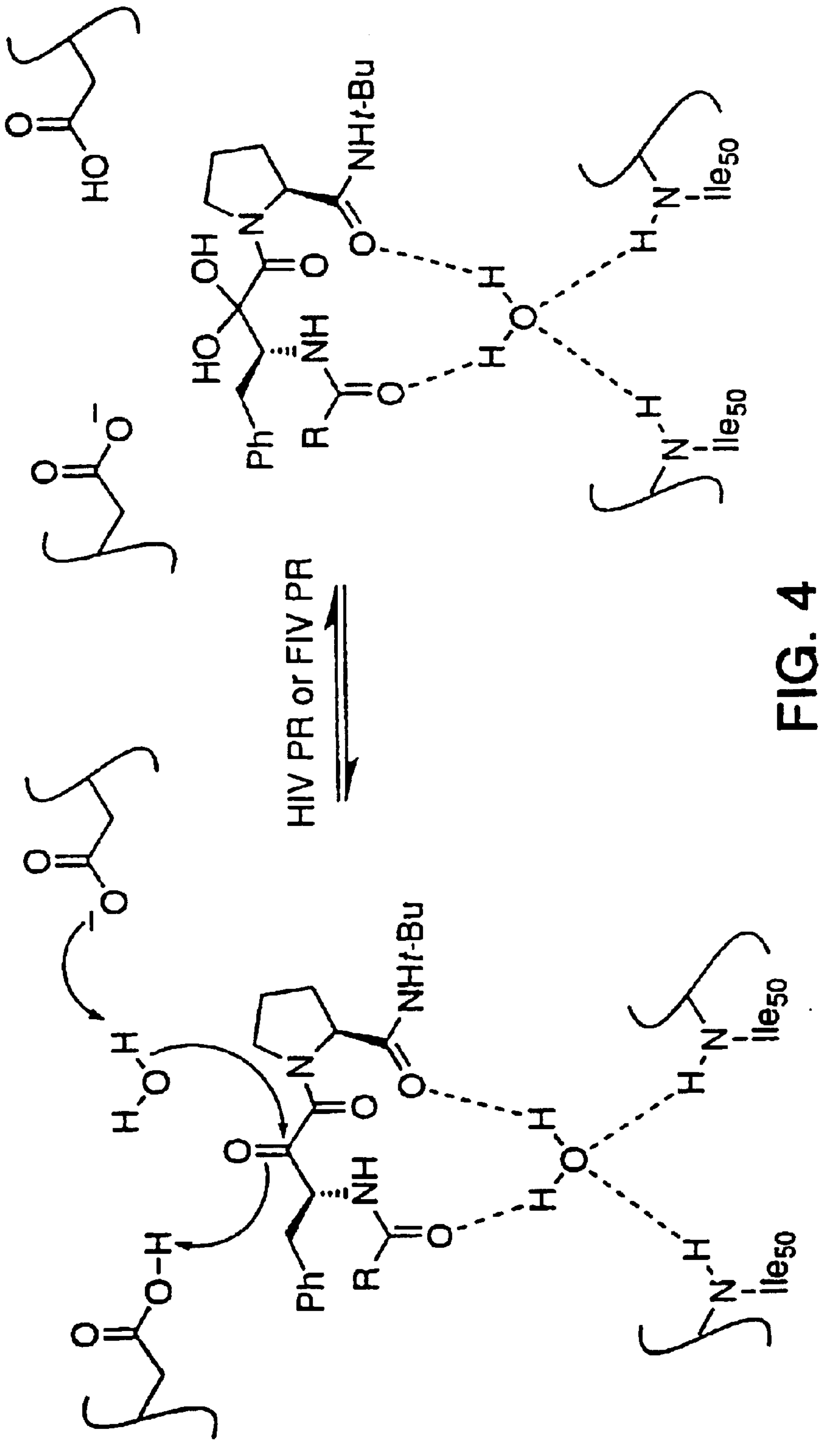
FIG. 4 shows the proposed mechanism of inhibition by 5b. A water molecule is added, with assistance of the enzyme, to the α-keto group to form a gem-diol.

Since the ketone moiety of 5b is not hydrated in aqueous solution according to $^{13}$C NMR studies, the increased inhibitory activity of 5b may occur via enzyme-assisted hydration of the ketone moiety within the active site to form a gem-diol as transition-state mimic, similar to the case of a related $\alpha$-keto amide inhibitor observed previously by x-ray structure and $^{13}$C NMR analyses (FIG. 4; Slee et al., ibid).

The relative inhibitory activities of inhibitors 2b–5b against FIV PR are similar to the relative activities against HIV PR. For example, 5b is a superior inhibitor of both enzymes, and the hydroxyketone 4b is 57- and 44-fold more effective than its diastereomer 3b against HIV and FIV PR, respectively. In addition, the relative effectiveness of the P1-P1' core structures in 2b–5b against HIV PR is also consistent with the binding pattern of their parent compounds 2a–5a. These results indicate that introduction of Val and Ala as P2 and P3 residues can improve the inhibition against both enzymes despite some changes for the P1-P1' core unit. In addition, extension of the backbone of an inhibitor to contain an appropriate P3 moiety is essential to exhibit high potency against FIV PR, which is also consistent with our previous results with C2-symmetric inhibitor 1b (Lee et al., ibid)

The kinetic results of inhibitors 6b and 7a, which were modified from existing drugs ABT-538 and RO31-8959 (Saquinavir), respectively were even more promising. Compound 7a was found to have $K_i$ values of 1.5 nM and 2.6 $\mu$M against HIV and FIV PR, respectively. The inhibitory activities of the original drug RO31-8959 were also evaluated under the same assay conditions, and found to have $K_i$ values of 1.6 nM and 76 $\mu$M for HIV and FIV PR, respectively. These results clearly indicated that compound 7a retained the original inhibitory activity of RO31-8959 against HIV PR, which was already optimized for the enzyme, but showed 29-fold enhanced potency against FIV PR. Inhibitor 6b also exhibited comparable activities to compound 7a, with $K_i$ values of 3.0 nM and 3.7 $\mu$M for HIV and FIV PR, respectively. However, compound 7b showed 7.5- and 51-fold less potent than 7a against HIV and FIV PR, respectively. Changing the P2 Val residue of 7a to Asn increased hydrophilicity of the inhibitor, which could be a major cause of lower activity found in 7b for both enzymes. In fact, compound 7b was more soluble in water than 7a and thus would require higher desolvation energy to bind the hydrophobic active sites of enzymes.

Figure 5A:
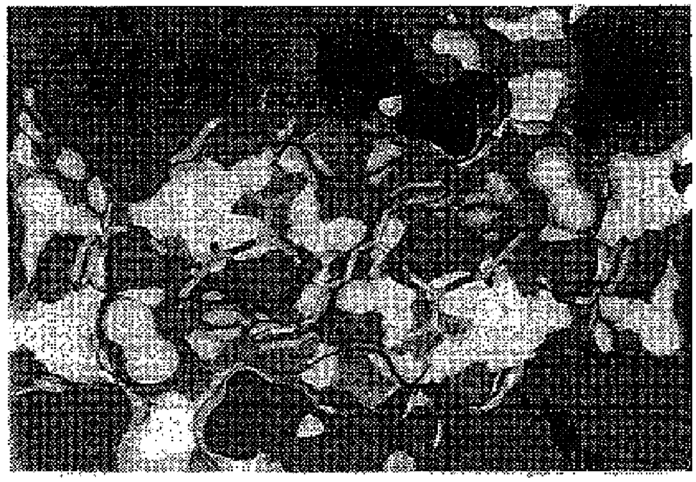
FIG. 5 illustrates models of HIV protease (top) and FIV protease (middle) complexed with RO31-8959, and FIV PR complexed with the modified inhibitor 7a (bottom). The P3 group of RO31-8959 is too big to fit the S3 subsite of FIV PR, whereas 7a with methyl group as P3 residue shows a good fit.
Figure 5B:
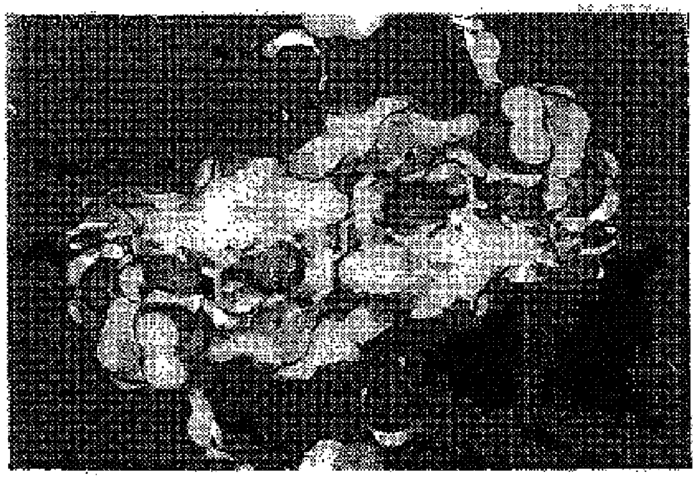
Figure 5C:

The above results suggest that inhibitors with a small P3 residue are effective against both FIV PR and HIV PR. These results are consistent with the results of molecular modeling which shows HIV and FIV PR binding to Saquinavir and its modified derivative with a small P3 residue (FIG. 5).

EXAMPLE 3

Inhibition of Drug-Resistant Mutant HIV PRs

The modified inhibitors with dual efficacy against FIV and HIV PR (1b, 4b, 5b, 6b, and 7a) were also tested against drug-resistant mutant HIV PRs G48V and V82F. These mutant enzymes were selected since Gly 48 and Val 82 are within the S3 and S3' subsites and have been identified as some of the most frequently mutated residues associated with development of drug resistance. Against these mutant enzymes, all modified inhibitors retained most of their original potency, and their relative inhibitory activity was also directly proportional to the efficacy against wild-type HIV PR. In particular, modification of the FDA approved drugs ABT-538 and RO31-8959 containing a bulky P3 group to the ones with methyl group at P3 (i.e. 6b and 7a) showed significantly improved inhibitory activity against the mutants, with only 4.8- and 6.5-fold higher $IC_{50}$ values for the V82F and G48V mutant variants, respectively, compared to 90- and 27-fold higher IC50 values for the parent compounds. It is noteworthy that V82F and G48V mutants are known to be less efficient enzymes compared to the wild-type HIV PR. Therefore, inhibitory activities of compounds tested against these mutant enzymes are expected to be lower compared to wild-type HIV PR. Compound 1b was also active in cell culture (Bacheler et al. J. Antiviral Chem. Chemother. 1994, 5, 111). The $IC_{90}$ values of 1b against the wild type HIV PR, the I84V and 82F/84V mutants are 0.1, 0.4 and 0.9 $\mu$M respectively.

EXAMPLE 4

C2-Symmetric Inhibitors with an iso-Butyl-2,3-diol Core as P1 and P1'

Since the side chains of P1 and P3 residues of 1b are positioned very close to each other in the S1 and S3 subsites of the enzyme, we have investigated the activities of new C2-symmetric inhibitors (8–11) with iso-butyl group at P1 and P1'. In addition, since water molecules were identified in the S3 and S3' subsites of both HIV and FIV PR complexed with 1b (The x-ray structure of 1b complexed with HIV, FIV (3X), FIV (V59I), and FIV (Q99V) PRs have been determined and will be published in Biochemistry), compounds (12, 13) containing a hydroxy group at P3 and P3' residues were synthesized with the hope that further improvement in inhibition would be obtained via favorable electrostatic interactions with the water molecule.

Figure 11:
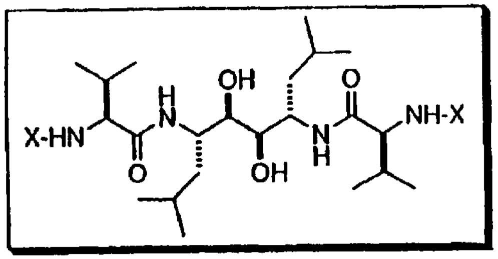
FIG. 11 tabulates the inhibition of FIV and HIV PRs by C2-symmetric diols wherein the superscript are each described as follows: Ki values were determined in duplicate. b) Data obtained at pH 5.25 at 370 C in 0.1M $NaH_2PO_4$, 0.1 M sodium citrate, 0.2 M NaCl, 0.1 mM DTT, 5% glycerol, and 5% DMSO in volume; c) data obtained at pH 5.25 at 370 C in 0.1M MES, 5% glycerol, and 5% DMSO in volume; d) From Slee et al. J. Am. Chem. Soc. 1995, 117, 11867–11878;nd, not determined.
Figure 11:
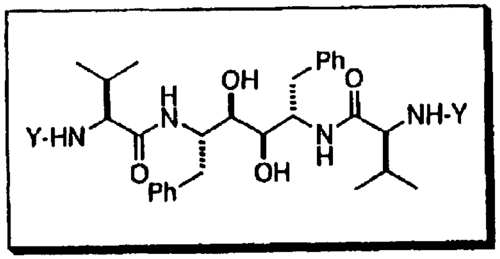

The inhibitory effects of each C2-symmetric inhibitor on HIV and FIV PRs were determined, and the results are recorded in FIG. 11. For comparison, the $K_i$ values for inhibition of FIV and HIV PR by the C2-symmetric inhibitors with a benzyl group at P1 and P1' are also included (1b, 9b–10b).

All the C2-symmetric diols tested in this study showed competitive inhibition of both the feline and human lentivirus PRs in every case, but with at least an order of magnitude higher potency against HIV PR. Among the inhibitors with iso-butyl groups at the P1-P1' core (8–11), compound 8 with Ala at P3 and P3' is the best inhibitor of FIV. This maximum inhibitory activity observed in compound 8 was reduced by increasing the size of the side chain of the P3 and P3' residues. In fact, the measured $K_i$ values of inhibitors 9, 10, and 11 were 3.7-, 7.9-, and 4-fold higher than 8.

This specificity for small hydrophobic groups at P3 and P3' sites found among the C2-symmetric inhibitors 8–10 with iso-butyl groups as the P1-P1' core against FIV PR was consistent with the observation for the analogous inhibitors 1b, 9b–10b. In addition, compounds 8 and 9 exhibited almost the same degree of potency against FIV PR compared to the benzyl analogs 1b and 9b, respectively. This result indicates that Leu can bind the S1 and S1' subsites of the enzyme as effectively as Phe. In the previous report, Lee et al. Proc. Natl. Acad. Sci. USA 1998, 95, 939–944, the explanation for the observed preference for small P3 and P3' moieties in FIV PR was that bulky groups at the P3 and P3' positions of the inhibitor could provoke unfavorable interactions at the sterically congested S3 and S3' subsites of FIV PR. In particular, compound 10b ($K_i$=7.0 μM) exhibited 170-fold lower potency than 1b. This proposal is still valid for the lower inhibitory activities of 9, 10, and 11 compared to 8 against FIV PR. However, it is noteworthy that compound 10 showed 14-fold higher inhibitory activity than its analog 10b. This improved potency against FIV PR observed in 10 can not be explained by the above proposal since both inhibitors contain Phe as P3 and P3' residues.

Therefore, current observations also suggest that the steric interaction between neighboring P1 and P3 side chains is another crucial factor to be considered for the design of new inhibitors. Indeed, compound 10, containing smaller P1 and P1' side chains than inhibitor 10b, can provide more room at S3 and S3' binding sites to accommodate bulky benzyl groups. This proposal was further confirmed by the modeling of FIV PR complexed with compound 8. The structure reveals that the side chain of P1 and P3 residues are positioned closely, and the combining S1 and S3 pocket is not wide enough to accommodate two benzyl groups. It is also expected that binding of P1 and P3 moieties can be affected by each other, and an appropriate combination of P1 and P3 residues is essential for good binding.

It has been determined that HIV PR exhibits a high degree of flexibility in binding at the S3 and S3' subsites (Lee et al., ibid). The results from the inhibition studies of the diols 8–10 against HIV PR showed very different patterns compared to their analogs 1b, 9b–10b. The $K_i$ values of compounds 8 and 10 were 4.3- and 2.0-fold higher than 1b and 10b, respectively. This indicates that Phe at P1 and P1' is better than Leu for binding to HIV PR. However, compound 9 is a more effective inhibitor than 9b and also showed 7.5- and 6.3-fold higher potency against HIV PR compared to 8 and 10, respectively. This significant improvement was not observed from 1b, 9b–10b. These kinetic results indicate that introduction of iso-butyl groups at S3 and S3' subsites can improve the potency of an inhibitor containing a medium size P1-P1' core, and suggest that the overall size of the P1 and P3 residues will affect significantly the binding specificity of the enzymes.

Finally, compounds containing a hydroxy group at P3 and P3' side chains (12 and 13) were also effective inhibitors of both HIV and FIV PR. In particular, compound 12 displayed the highest potency with $K_i$ values of 0.58 nM and 32 nM against HIV and FIV PRs, respectively. It is noteworthy that compound 12 is more hydrophilic than 1b by two additional hydroxy groups and would require more desolvation energy in order to bind to the hydrophobic active sites of enzymes. However, compound 12 exhibited a 3-fold higher potency against HIV PR and similar inhibition against FIV PR, compared to 1b. These results indicate that binding of 12 is significantly enhanced by the two hydroxyl groups of the P3 and P3' side chains, presumably by promoting favorable electrostatic interactions with the crystallographic water molecules at the S3 and S3' subsites. The ability of 12 to prevent infection of FIV in tissue culture was also examined. It was, however, not as effective as 1b. It has been known that introduction of hydrophilic functional groups, such as a hydroxyl or carboxyl group, to the P2 and P2' positions of C2-symmetric inhibitors would cause a dramatic loss of potency against HIV PR in tissue culture, though the inhibitory activity in vitro has little change (Budt et al. Bioorg. Med. Chem. 1995, 3, 559–571). Our ex vivo assay results have confirmed a similar activity loss in tissue culture by the presence of a hydrophilic group at P3 and P3'. These results suggest that increasing the overall polarity and hydrophilicity of compounds may result in the reduction of efficacy in vivo.

The above results indicate that the interaction of P1 and P3 residues in the active sites of HIV and FIV PR is a crucial factor to be considered for maximizing the binding affinity of inhibitors. Although it has been considered that Phe can provide ideal binding at the S1 subsite of HIV PR, our observations suggest that with appropriate P3 and P3' moieties, one can also develop potent inhibitors with P1 and P1' side chains smaller than the benzyl group.

EXAMPLE 5

Synthpsis of Key Intermediates and Inhibitors

Figure 6:
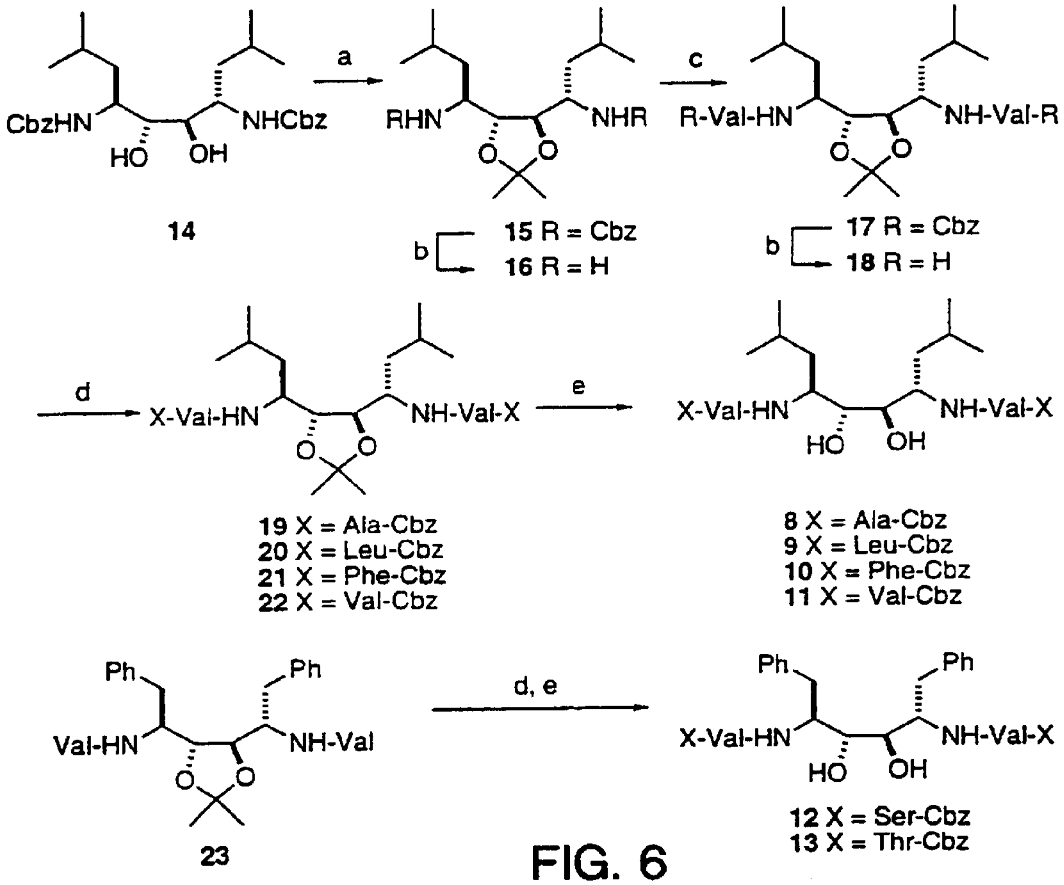
FIG. 6 shows the synthesis of intermediate compound 13 with the following conditions: (a) 2,2-dimethoxypropane, p-TsOH (80%); ;(b) Pd/C, H2, MeOH (99%); (c) HBTU, Cbz-Val, Et3N, CH3CN (89%); (d) HBTU, Cbz-amino acids, Et3N, CH3CN; (e) p-TsOH, MeOH.

The key intermediates (1S,2R,3R,4S)-1,4-bis[(N-Cbz)amino]-1,4-dibenzyl-2,3-diol and (1S,2R,3R,4S)-1,4-bis[(N-Cbz)amino]-1,4-diisobutyl-2,3-diol 14 (Scheme 1) were prepared by the stereoselective Pinacol coupling of L-Cbz-phenylalanal and L-Cbz-leucinal, respectively, using Pedersenis procedure (Konradi et al. J. Org. Chem. 1992, 57, 28–32). The minor diastereomeric impurities of the coupling reaction were removed by flash column chromatography after protection of the diol as an isopropylidene derivative (15). The Cbz groups of compound 15 were removed to yield the diamine 16 by hydrogenation. Amine 16 was directly coupled with Cbz-Val using HBTU to give adduct 17 (Dourtoglou et al. Synthesis 1984, 572–574). Four different P3 and P3' residues were then introduced to adduct 17 by applying the same deprotection and coupling procedures described above to give compounds 19–22. Finally, the target inhibitors 8–11 were prepared by deprotection of the isopropylidene group from the corresponding precursors (FIG. 6). Compounds 12 and 13 were obtained by applying the same procedure described previously using (1S,2R,3R,4S)-1,4-bis[(N-Cbz)amino]-1,4-dibenzyl-2,3-diol as a starting material.

Figure 7:
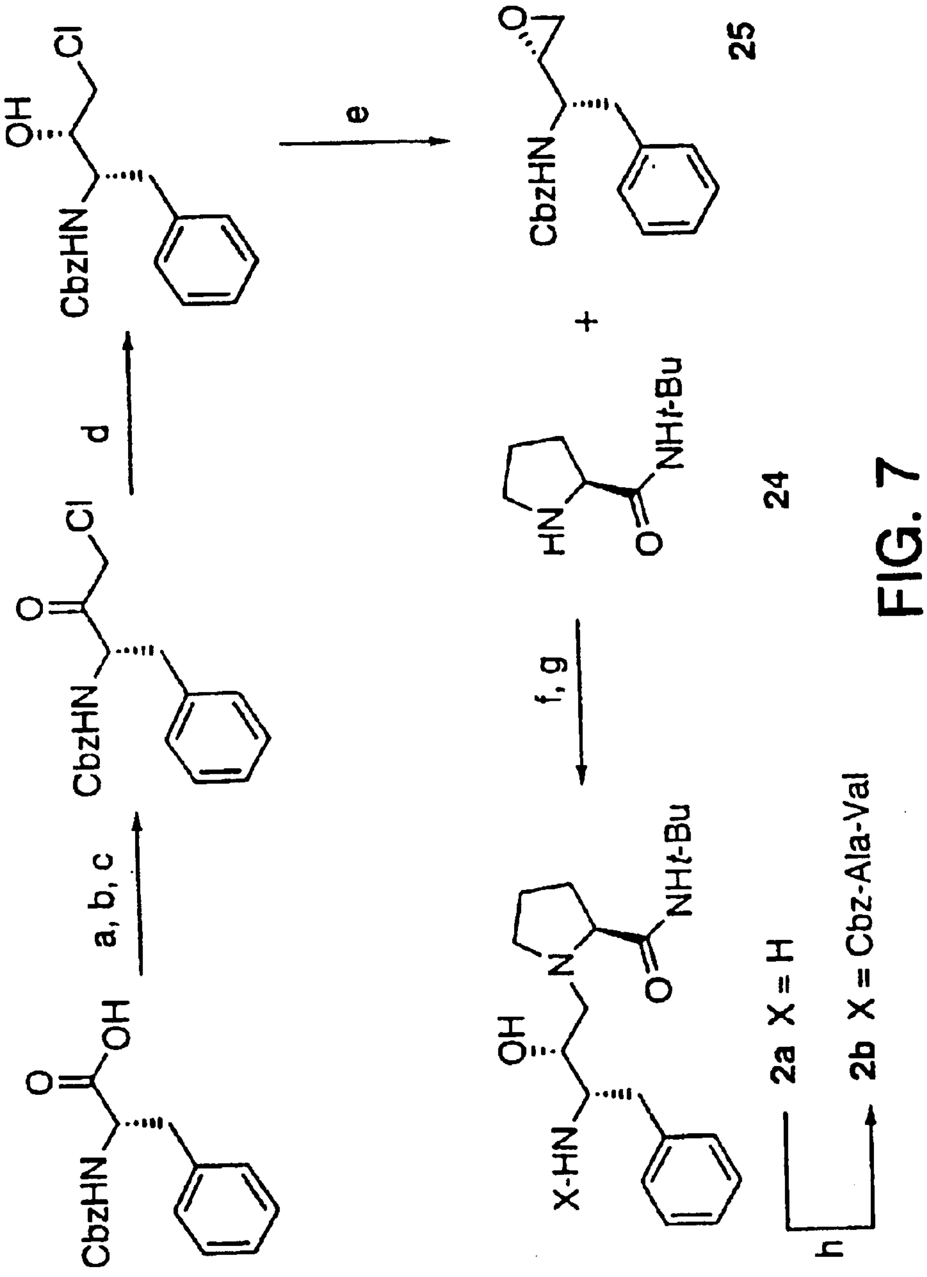
FIG. 7 shows the synthesis of compound 2b with the following conditions: (a) NMM, THF, i-BuOCOCl. (b) CH2N2, $Et_2O$. (c) HCl (85%, 3 steps) (d) $NaBH_4$, EtOH, (90% d.e, 81%) (e) NaOMe, MeOH (96%). (f) MeOH, $Et_3N$ (90%)(g) Pd/C, $H_2$, EtOAc. (h) Cbz-Ala-Val-OH, HBTU, $Et_3N$, $CH_3CN$. (49%, 2 steps).

The hydroxyethylamine inhibitor 2b was prepared by coupling the proline derivative 24 to the epoxide 25 (Slee et al. J. Am. Chem. Soc. 1995, 117, 11867–11878; Hung et al. J. Org. Chem. 1991, 56, 3849–3855) via reflux in methanol, using triethylamine as shown in FIG. 7. The synthesis of the core isostere 5a has been modified from the method previously employed by our group. The α-hydroxy acid 26, prepared from known procedures (Munoz et al. Bioorg. Med. Chem. 1994, 2, 1085–1090) was coupled to the proline derivative 24 to give the α-hydroxy amides 3a and 3b. Hydrogenation of the diasteromers 3a and 3b followed by HBTU mediated coupling with Cbz-Ala-Val-OH gave 4a and 4b in 65% yield. Dess-Martin oxidation of the α-hydroxy amides 3a–4b gave the corresponding α-keto amides 5a and 5b in moderate yield (FIG. 8; Dess, D. B.; Martin, J. C. J. Am. Chem. Soc. 1991, 113, 7277–7287).

Figure 9:
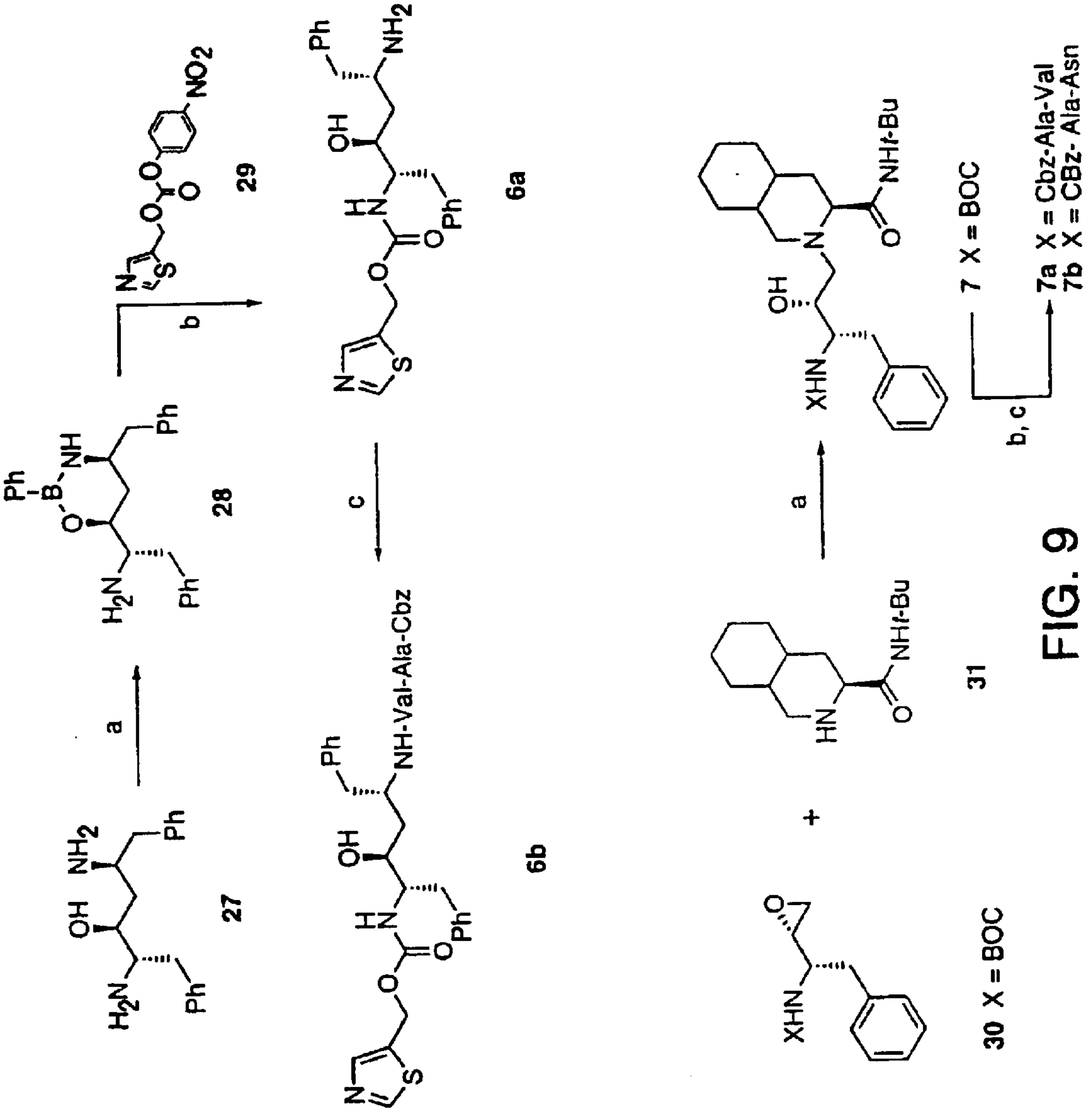
FIG. 9 illustrates the synthesis of the modified existing drug 6b with the following conditions: (a) $PhB(OH)_2$, PhMe, reflux (b) THF, rt, (78%, 2 steps); (c) Cbz-Ala-Val-OH, HBTU, $Et_3N$, $CH_3CN$ (73%); and drugs 7a,b with the following conditions: (a) MeOH, $Et_3N$, (80%). (b) TFA, $CH_2Cl_2$. (c) HBTU, $Et_3N$, $CH_3CN$, Cbz-Ala-Val-OH (76%) or Cbz-Ala-Asn-OH (78%).

The synthesis of 6b began with the cyclic boronate 28 prepared by refluxing the diamine 27 with phenylboric acid (Kempf et al. J. Med. Chem. 1998, 41, 602–617). Condensation of the phenyl boronate 28 with carbonate 29 followed by HBTU mediated coupling with Cbz-Ala-Val-OH gave the desired product 6b (FIG. 9). The synthesis of the modified Saquinavir™derivatives 7a and 7b began with condensation of the isoquinoline derivative 31 with epoxide 30 to give the adduct 7 in 80% yield (Thompson et al. J. Am. Chem. Soc. 1993, 115, 801–803). Removal of the BOC group in 7 with TFA followed by HBTU coupling with Cbz-Ala-Val-OH or Cbz-Ala-Asn-OH gave the modified inhibitors 7a and 7b respectively (FIG. 9).

In summary, manipulation of the backbone of HIV PR inhibitors to create appropriate P3 residues can improve potency against FIV, HIV, and mutant HIV PRs, regardless of the structure of the P1-P1' core units. The inhibitors with small P3 and bulky P1 described in this study are effective against FIV and HIV PR, and exhibit high potency against drug-resistant mutant HIV PRs. In addition, modification of some existing HIV PR inhibitors to have a small P3 group also enhances their inhibition of FIV PR and mutant HIV proteases without affecting the activity against wild-type HIV PR. The development of broad-based inhibitors described in this study contributes significantly to our understanding of the specificity and resistance development of the aspartyl protease and provides a new strategy for the development of new antiviral pharmaceuticals.

Although the current results represent only an initial step toward development of therapeutic agents efficacious against both native and mutant HIV proteases, using FIV PR as a general model for the drug-resistant mutant HIV PRs is clearly an effective strategy. One may thus use cats as a drug-resistant animal model to accelerate the new drug development process.

EXAMPLE 6

Analysis of the S3 and S3' Subsite Specificities of FIV Protease: Development of a Broad-based Protease Inhibitor Efficacious Against FIV, SIV, and HIV in vitro and ex vivo The S3 and S3' subsite binding specificities of HIV and FIV PRs have been explored using $C_2$-symmetric competitive inhibitors. The inhibitors evaluated contained (1S,2R, 3R,4S)-1,4-diamino-1,4-dibenzyl-2,3-diol as P1 and P1' units, Val as P2 and P2' residues, and a variety of amino acids at the P3and P3' positions. All inhibitors showed very high potency against HIV PR in vitro, and their $K_i$'s ranged between 1.1 and 2.6 nM. In contrast to the low restriction of P3 and P3' residues observed in HIV PR, FIV PR exhibited strong preference for small hydrophobic groups at the S3 and S3' subsites. Within this series, the most effective inhibitor against FIV PR contained Ala at P3 and P3'. Its $K_i$ of 41 nM was 415- and 170-fold lower than those of the inhibitors without the P3 and P3' moieties or with the Phe at these positions, respectively. In addition, these compounds were tested against mutant FIV PRs, which contain amino acid substitutions corresponding to those in native HIV PR at homologous sites, and their efficacy of inhibition progressively increased up to 5-fold. The most potent FIV PR inhibitor was selected for examination of its effectiveness in tissue culture, and it was able to block nearly 100% of virus production in an acute infection at 1 μg/ml (1.1 μM) against HIV, FIV and SIV. Furthermore, it was not toxic to cells, and even after 2 months of culture there was no sign of resistance development by virus. The findings suggest that the more stringent requirements for FIV PR may lead to the development of broad-based inhibitors that will be efficacious against a broad range of HIV quasispecies as well as interspecies PRs.

Figure 13:
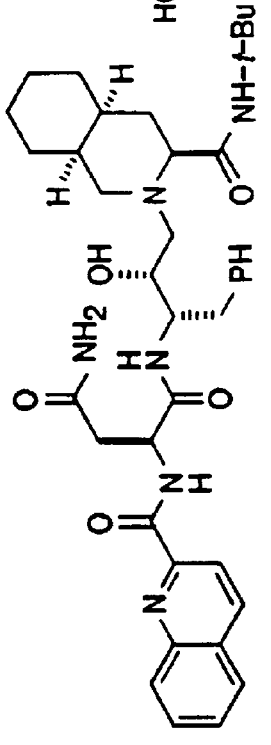
FIG. 13 illustrates examples of HIV PR inhibitors testes as inhibitors of FIV PR.
Figure 13:
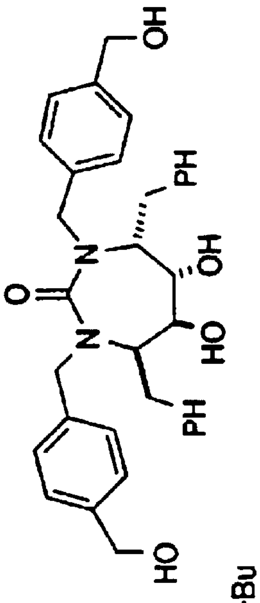
Figure 13:
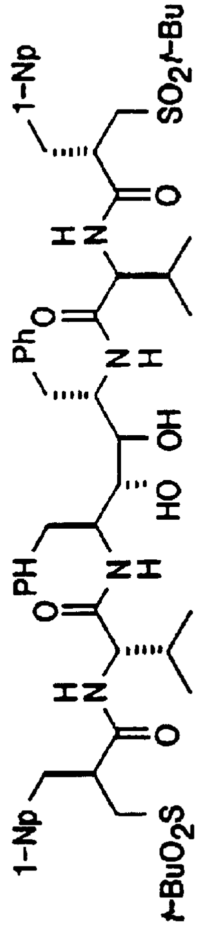
Figure 13:
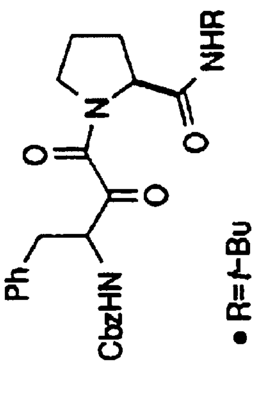

At least six mutated residues in HIV PR which cause drug resistance are also found in the structurally aligned native residues of FIV PR. Kinetic studies also showed that various potent HIV PR inhibitors containing the P3 to P3' residues Slee et all, JACS 117, 11867–11878, including the FDA approved drug Ro 31–8959 (ibid), are less efficient inhibitors of FIV PR by a factor of 100 or more. Although the significance of these observations is yet to be appreciated, it suggests that FIV PR may serve as a model for drug resistant mutant HIV PRs and may contribute to the understanding of HIV resistance to protease inhibitors. Therefore, we are developing potent inhibitors of FIV PR containing residues which bind to the S3 to S3' region with the aim of developing broad-based therapeutic agents against AIDS which may be less prone to resistance development. Additional advantage of this strategy, if effective, is to facilitate the in vivo testing of candidate inhibitors in an animal system (FIG. 13).

Since the active sites of both HIV and FIV PRs are C2-symmetric, it has been predicted that the axis of symmetry of an inhibitor with a C2-symmetric unit would coalign with the C2-axis of the enzymes resulting in specific inhibition. In fact, C2-symmetric inhibitors containing diol cores have been identified as extremely potent inhibitors of HIV PR in vitro. The x-ray crystal structure of HIV PR complexed with the inhibitor A-76889, containing (1S,2R, 3R,4S)-1,4-diamino-1,4-dibenzyl-2,3-diol as P1 and P1' unit and N-protected Val as P2-P3 and P2'-P3', also displayed the high degree of structural correspondence at P1-P3, P1'-P3' although the R,R diol core bound in an asymmetric mode Condra et al., 1995 Nature, 374, 69–571. Therefore, evaluating the binding affinities of C2-symmetric inhibitors represents a convenient strategy for systematic probing of enzyme specificities at certain sites. The kinetic parameters of the FIV PR for peptide substrates also indicated that replacing Val at P2 position by Ile led to a significant decrease in binding. Therefore, compound 500 (FIG. 12) was chosen as a core unit. A variety of amino acids were then introduced to the core as the P3 and P3' residues by a combinatorial approach to rapidly create a number of potential inhibitors for the analysis of amino acid restriction and tolerance at the S3 and S3' subsites of HIV and FIV PRs. Promising compounds revealed by in vitro analyses were then tested ex vivo for efficacy against FIV, SIV, and HIV if infection.

Chemical Syntheses.

Figure 12:
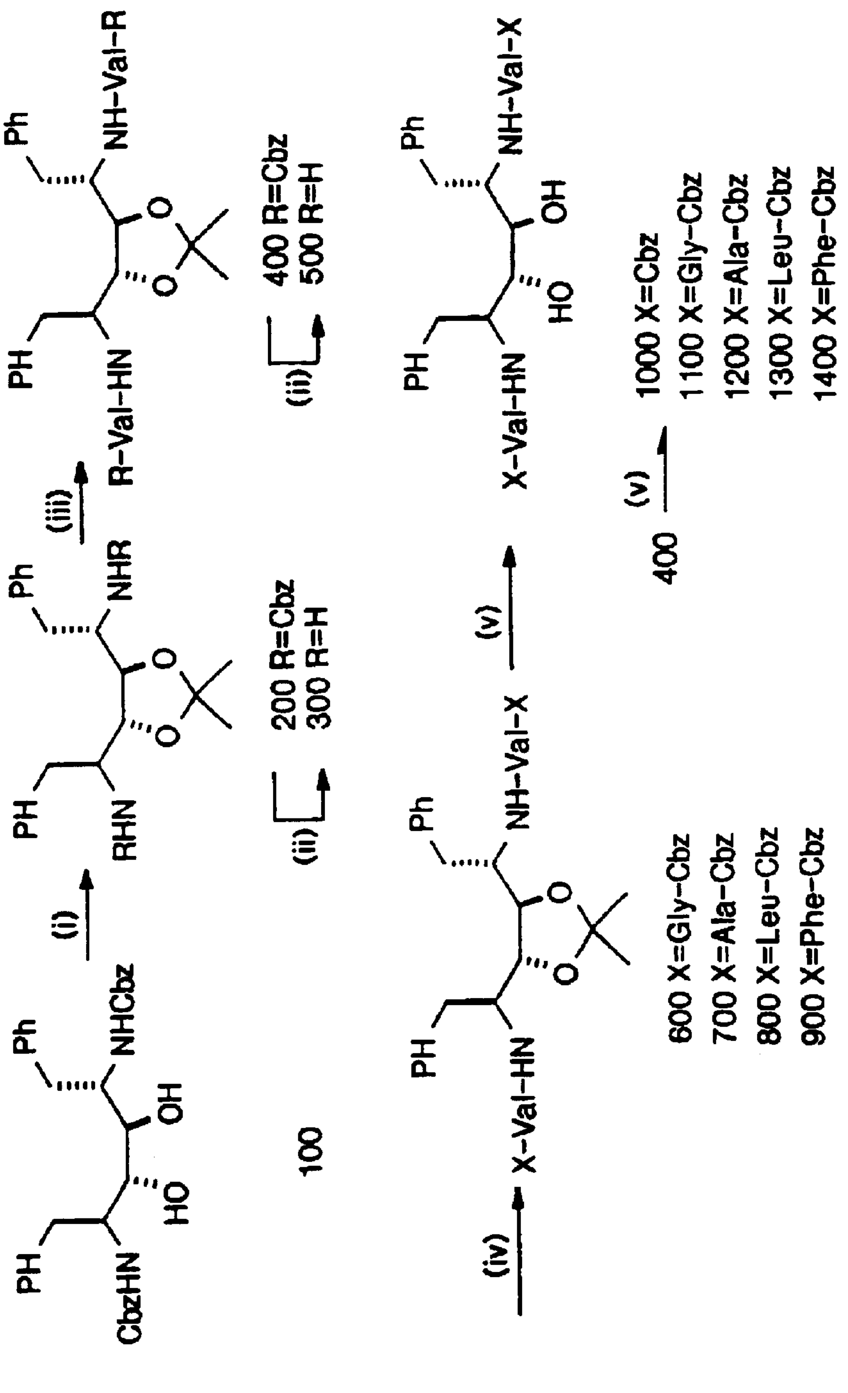
FIG. 12 illustrates the synthsis of $C_2$ symmetric inhibitors 1000–1400.

The (1S,2R,3R,4S)-1,4-bis[(N-Cbz)amino]-1,4-dibenzyl-2,3-diol 100 was prepared by PedersenÔs procedure Konradi et al J. Org. Chem 57, 28–32, along with its diastereomers. After protection of the diol as the isopropylidene 200, these minor diastereomeric impurities were removed by flash column chromatography. The Cbz groups of compound 200 were deprotected by hydrogenation, then the diamine 300 was coupled with Cbz-Val using HBTU providing adduct 400. Four different P3 and P3' residues were then introduced to adduct 400 by applying the same deprotection and coupling procedures described above to give compounds 600–900. Finally, the target inhibitors 1100–1400 were obtained by removal of the isopropylidene from the corresponding precursor under acidic conditions. The same procedure was applied in the synthesis of other compounds which were not shown here (Wlodawer et al, 1995, Nat. Struc. Biol. 2, 480–488). The reference inhibitor 1000 was also synthesized from compound 400 by the same deprotection procedure (FIG. 12).

In Vitro inhibitory Activities Against Proteases.

The inhibitory effects of each inhibitor were evaluated against HIV and FIV PRs along with two mutant FIV PRs that contain amino acid substitutions corresponding to those in HIV PR at homologous sites. The results of some selective inhibitors, each of which is a competitive inhibitor of all four enzymes, are summarized in FIG. 17.

All the $C_2$-symmetric diols tested in this study showed very high potency against HIV PR, and their $K_i$'s ranged between 1.1 and 2.6 nM. Considering experimental error, there was no significant difference in the overall efficacy of these diols in inhibition of HIV PR. In part, this reflects the low restriction of amino acid residues at the S3 and S3' subsites of HIV PR. In addition, the Cbz groups of the reference inhibitor 1000, which does not contain P3 and P3' residues, could be positioned tightly at the S3 and S3' subsites of HIV PR to make compound 1000 an effective inhibitor. However inhibition of FIV PR by inhibitors 1000–1400 showed a remarkably different pattern. First, the inhibitory activity of the reference compound 1000 was decreased by almost $1.7\times10^4$ fold compared to its $K_i$ for HIV PR. This striking activity loss observed for 1000 was recovered by extending the backbone of the inhibitor using Gly as P3 and P3' residues, with the $K_i$ of 1100 being 110 fold lower than 1000. This preference of the extended inhibitor backbone found in FIV PR is also supported by the observation that HIV PR will cleave a six residue peptide substrate, Ac-Gln-Ala-Tyr-Pro-Ile-Gln (SEQ ID NO: 2), whereas the smallest FIV PR substrate is an eight residue peptide, Ac-Pro-Gln-Ala-Tyr-Pro-Ile-Gln-Thr (SEQ ID NO: 1). The best residue for S3 and S3' binding was Ala. In fact, inhibitor 1200 ($K_{i=41}$ nM) is the most potent inhibitor of FIV PR known to date. The inhibitory activity of 1200 against FIV PR was reduced. by increasing the size of the side chain of the P3 and P3' residues, with the $K_i$ of 1300 4-fold higher than 1200. Furthermore, the diol 1400 showed 45- and 170-fold lower potency compared to 1100 and 1200, respectively, and this result suggests that the benzyl side chain of P3 and P3' may cause unfavorable interaction with FIV PR or the neighboring P1 and P1' side chains. This severe restriction of P3 and P3' moieties in FIV PR partly explains the total loss of potency against FIV PR by HIV PR inhibitor Ro 31-8959, since it contains bulky aromatic group at the P3 position.

The result was further confirmed by comparison of the x-ray structures of FIV and HIV PRs complexed with inhibitors. The structures revealed that only two residues (Arg 13, Asp 34) in the S3 and S3' subsites of FIV PR were conserved at the structurally aligned HIV PR positions. Three other residues at the subsites Gly 48, Pro 81, and Val 82 of HIV PR were replaced with Ile 57, Ile 98, and Gln 99 in FIV PR. As a result, the S3 and S3' subsites of FIV PR is sterically more congested than those in HIV PR, and these three different residues may define the S3 and S3, subsite specificities of the enzymes. In addition, the Gly 48 and Val 82 of HIV PR have been identified as frequently mutated residues to develop drug resistance. For example, the potency of the FDA approved drugs containing bulky P3 moieties, Ro 31-8959 and ABT-538, against G48V mutant was decreased by 27 and 17 fold, respectively. Among the HIV PR variants containing mutations at Val 82, the V82F mutant becomes 15, 7, and 90 fold less sensitive toward the licensed drugs AG-1343, MK-639, and ABT-538, respectively. It is noteworthy that both AG-1343 and MK-639 contain no P3 residues. Restrictions observed in mutant HIV PRs with inhibitors containing inappropriate P3 and P3¢ moieties are very similar to binding preferences found in FIV PR. These observations further support utility of FIV PR as a model for drug resistant variants.

The results from the inhibition studies of the diols 1000–1200, 1400 against the mutant FIV PRs are also intriguing. The less effective inhibitors 1000 and 1400 showed very similar activities against mutants compared to wild type FIV PR. However, the efficacy of inhibition by the more potent inhibitors 1100 and 1200 was progressively increased up to 5 fold in mutant enzymes. Overall, these results provide new insights into the specificity and resistance development of the aspartyl proteases and may help development of new inhibitors better than those which are currently available as described above.

Ex Vivo Inhibitory Activities of Compound 1200.

The ability of the most potent FIV PR inhibitor 1200 to prevent infection of FIV, HIV and SIV in tissue culture was examined. The results are summarized in FIG. 14.

Figure 14:
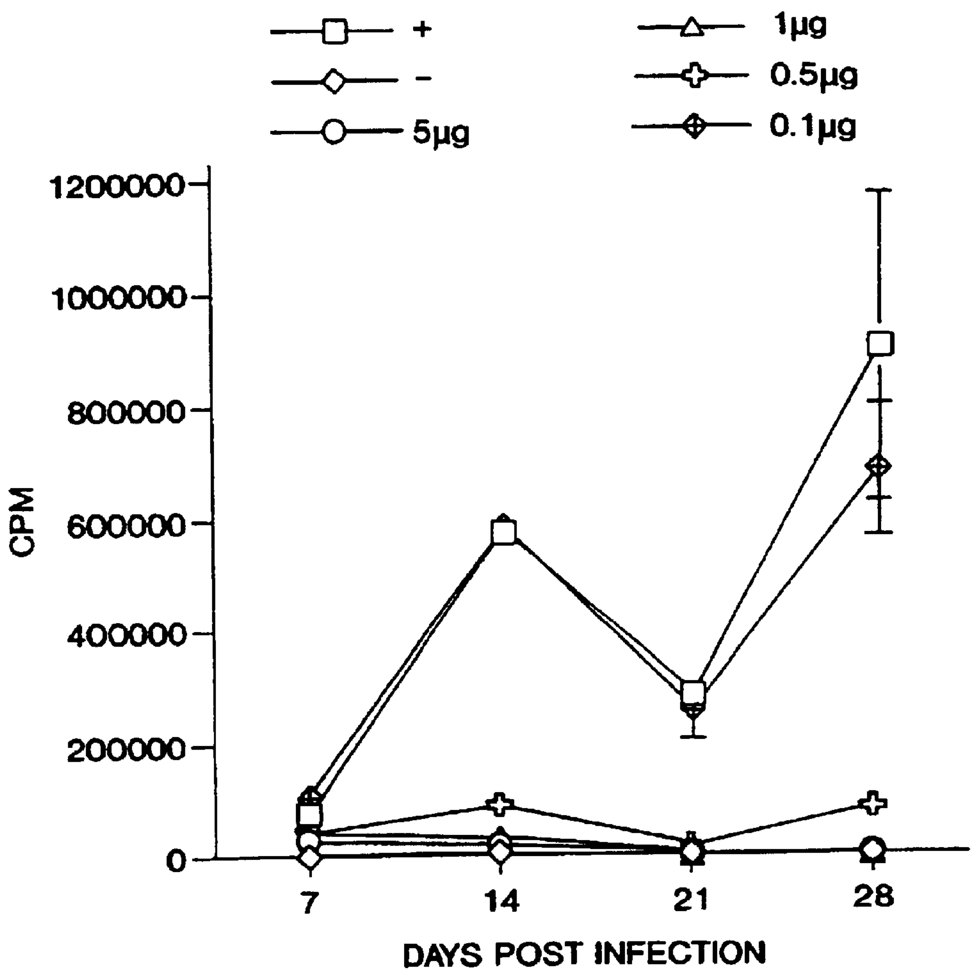
FIG. 14 illustrates TL-3-139 Timecourse PPR-FIV Acute Infection.
Figure 15:
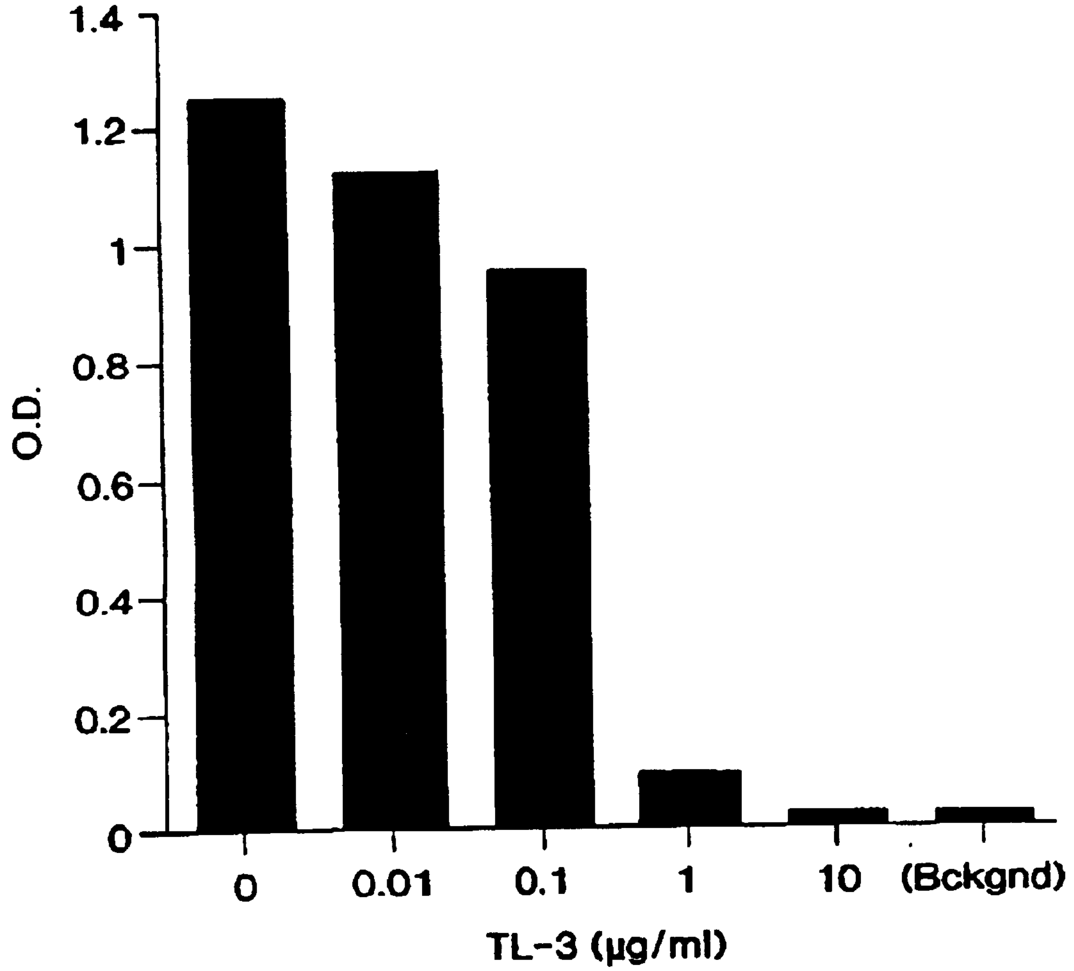
FIG. 15 illustrates SIV p27 ELISA.
Figure 16:
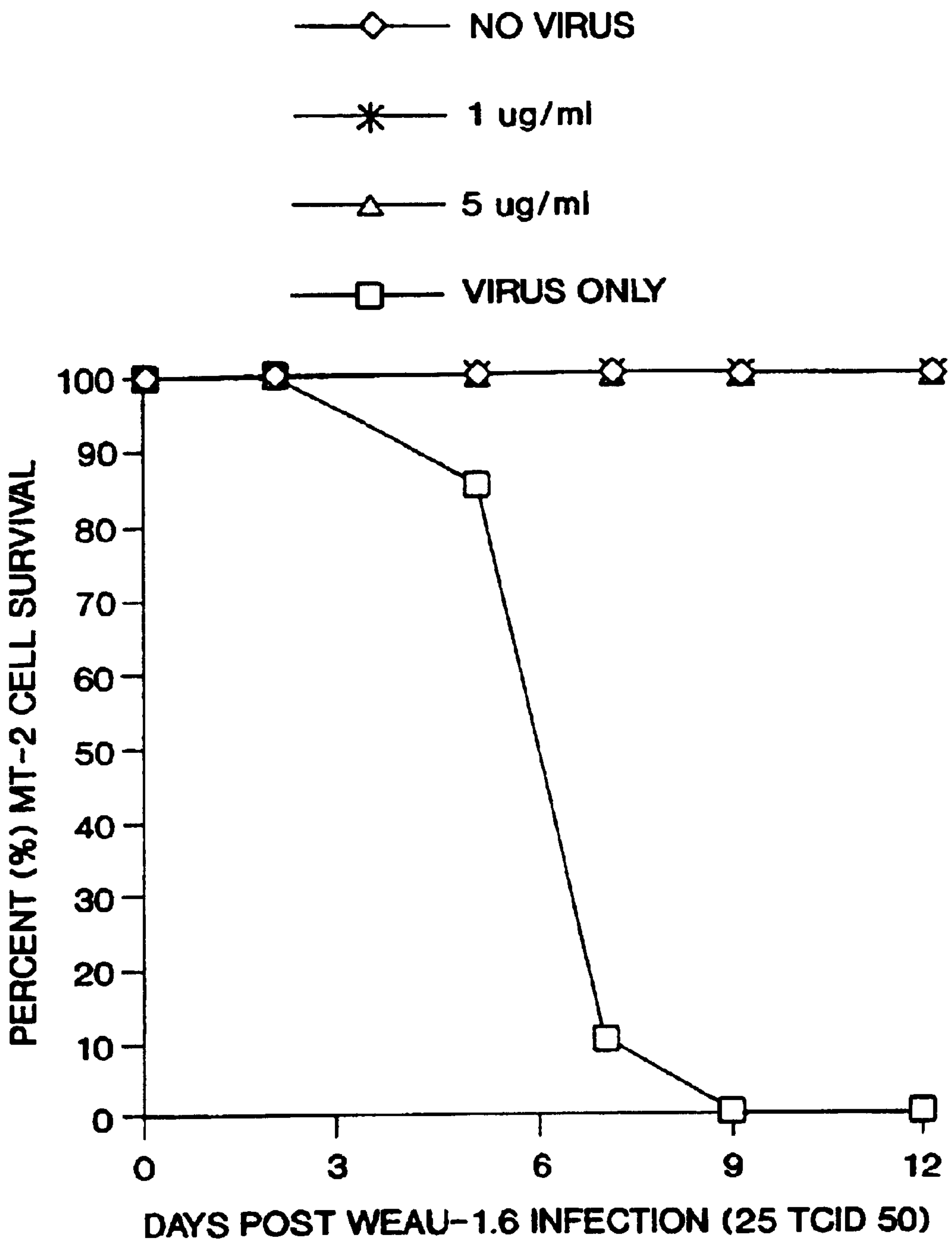
FIG. 16 shows Days post WEAU-1.6 Infection (25 TCID 50).

For FIV, the assays were performed in FIV-infected feline T-cells which were cultured in the presence of compound 1200 at different concentrations over the course of 1 month. Each data in FIG. 14 represents the amount of pelletable FIV reverse transcriptase in the culture supernatant. Compound 1200 was able to markedly inhibit FIV replication at 0.5 μg/ml (0.55 mM) and found to be most effective at 1.0 μg/ml (1.1 μM). Furthermore, this inhibitor was not toxic to feline T-cells. After one month, the drug-treated cultures were split and replated with and without compound 1200. No virus was detected in the absence or presence of drug after two weeks in culture (Not shown). No sign of resistance development against the drug has been observed after eight weeks of continuous culture.

The results from tissue culture assays against SIV (FIG. 14) and HIV (FIG. 14) were equally encouraging. Compound 1200, at 1 μg/ml, reduced virus expression levels to near background, as judged by reduction in release of p27 antigen into the culture supernatant in the presence of drug. The effectiveness of compound 1200 against HIV was measured by determining the percentage of viable cells remaining in culture over time in the presence and absence of drug (FIG. 14). In the control, HIV caused formation of multinucleated syncytia and 100% cell death by 9 days post infection. However, the cells cultured with 1 μg/ml (1.1 μM) or 5 μg/ml (5.5 μM) of inhibitor 1200 remained 100% viable after 1 month, identical to results obtained in the absence of virus infection. To test for virus in these cultures, supernatants were removed and added to $1\times10_5$ uninfected MT-2 cells after a 1:5 dilution with fresh CM. After 3 weeks the MT-2 cells remained uninfected, demonstrating the absence of free virus in cultures of infected MT-2 cells treated with compound 1200. In contrast, when $2\times10_5$ infected MT-2 cells that had been treated with compound 1200 for two weeks were removed and replated in fresh medium with or without compound 1200 only MT-2 cells cultured in the absence of compound 1200 were dead within 4 days (data not shown). These results clearly demonstrated strong potency of the drug against HIV as well as minimal toxicity to host cells. Cultures are being carried continuously in the presence of compound 12 to look for resistance development. Tests are also underway to determine the level of efficacy of the compound against a defined panel of drug-resistant HIVs.

It is clear that FIV PR exhibits a specific preference for amino acids containing small side chains at the P3 and P3' positions, especially for Ala. In addition, extension of inhibitor backbone can increase the potency of inhibitors in FIV PR. Our in vitro inhibition studies of mutant FIV PR also showed a direct relationship between the inhibition of FIV PR and HIV PR. This observation suggests that potent inhibitors of FIV PR, containing P3 to P3' residues, become even more efficient against HIV PR.

The most potent inhibitor 1200 has also shown strong ability to control lentiviral infections in tissue culture. In fact, this is the first compound which inhibits replication of FIV, HIV and SIV with virtually the same degree of effectiveness. This remarkable versatility of compound 1200 also suggests the strong possibility of sustaining its potency against mutant HIV PRs. Experiments are underway to test this hypothesis. Finally, while the current results represent only an initial step toward developing potential therapeutic agents against HIV PR which will be effective against native protease as well as mutant enzymes, using the FIV system for advancing HIV therapies is clearly an effective and relevant strategy where target drugs have dual efficacy against FIV and HIV. As a natural animal system, FIV offers the ability to perform in vivo tests of efficacy and assessment of drug resistance that is not readily feasible in primate systems. In addition, it is hoped that the broad-based nature of inhibitors arising from these studies will afford a reduced level of resistance development.

While a preferred form of the invention has been shown in the drawings and described, since variations in the preferred form will be apparent to those skilled in the art, the invention should not be construed as limited to the specific form shown and described, but instead is as set forth in the following claims.

Synthetic Protocals

General Procedures:

Analytical TLC was performed on pre-coated plates (Merck, silica gel 60F-254). Silica gel used for flash column chromatography was Mallinckrodt Type 60 (230–400 mesh). NNR ($^1H$, $^{13}C$) spectra were recorded on either a Bruker AMX-400 or Am-500 MHz fourier transform spectrometer. Coupling constants (J) are reported in hertz (Hz), and chemical shifts are reported in parts per million (δ) relative to tetramethylsilane (TMS, 0.0 ppm) with $CDCl_3$, DMSO or $CD_3OD$ as solvent. All other reagents were commercial compounds of the highest purity available and purchased from the Aldrich, Sigma, Nova Biochem, or Bachem. It should be noted that "x" as shown in the FIG. 3 is selected from the group consisting of hydrogen, carbobenzyloxy-, carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-alanine-asparagine-, carbobenzyloxy-threonine-valine- and carbobenzyloxy-valine-valine- all linked to the inhibitors using the procedures as described below and wherein all groups obtained from sources disclosed above or synthesized using procedures well known in the art or stated herein.

Molecular modeling:

Models of the protease inhibitor, 1b, complexed with HIV-1 protease and.FIV protease were built using the Brookhaven Protein Data Bank entries 1HVI11 and 1FIV6 as starting points. The entry 1HVI has a resolution of 1.8≈, and contains the C2-symmetric Abbott inhibitor A77003 (R, S) co-crystallized with the HIV-1 protease of strain HIVLAI expressed in *E. coli*. The structure of A77003 is quite similar to that of 1b. The stereochemistry of one of the ёcoreí hydroxyls had to be inverted, and the pyrimidine groups were replaced by the Cbz groups. The 1FIV structure has a resolution of 2.0≈ and contained the inhibitor LP-149 co-crystallized with the Feline immunodeficiency virus protease from Felis catus and expressed in *E. coli.*

The model of 1b bound to HIV-1 protease was built first, using InsightII 97.0ís Biopolymer18 and Discover modules, and the AMBER force field. Molecular mechanics minimization was performed using the conjugate gradients minimizer until the minimization converged, i.e. the derivative of the energy was less than 0.001. Distance constraints were used in the early stages of the modeling to ensure that the hydrogen bonds were preserved between the inhibitor, water and protease. Initially, only the inhibitor model, five active-site water molecules, and the residues of the active site that were in contact with the inhibitor were allowed to move. These five waters were the water bound between the tips of the flaps, and four waters, two in each sub-unit of the dimer, that bind inside a pocket adjacent to the the Arg-8 residue in HIV (Arg-13 in FIV). The resulting model was minimized while allowing all atoms to move. A similar procedure was applied to the modeling shown in FIG. 5, using HIV protease complexed with RO31-8959.

1) Biological Assays

For determination of $IC_{50}$ values for HIV protease, a backbone engineered HIV-1 protease, prepared by total chemical synthesis (Kent et al. Science 1992, 256, 221) 450 nM final concentration was added to a solution (152 μL final volume) containing inhibitor, 28 μM fluorogenic peptide substrate (sequence Abz-Thr-Ile-Nle-Phe-(p-$NO_2$)-Gln-Arg-$NH_2$ (SEQ ID NO: 3) (Toth et al., Int. J. Peptide Res. 1990, 36, 544)) and 1.8% dimethylsulfoxide in assay buffer: 100 nM MES buffer containing 0.5 mg/mL BSA (Bovine Serum Album, fatty acid, nuclease and protease free—to stabilize enzyme) at pH 5.5. The solution was mixed and incubated over 5 minutes during which time the rate of substrate cleavage was monitored by continuously recording the change in fluorescence of the assay solution. An excitation filter of 325 nm, and an emission filter of 420 nm were used. This data was converted into μM substrate cleaved per minute, using a predetermined standard calibration curve of change in fluorescence against concentration of substrate cleaved.

Determination of $K_i$ for HIV protease was performed similarly with the following modifications. The substrate concentrations used were 57, 43, 28 and 14 μM. All other concentrations were as above. The curve fit for the data was determined and the subsequent $K_i$ derived using a computer program based on the equation of Morrison et. al. BioChim. Biophys. ACTA 1969,185, 269, for tight binding inhibitors.

For determination of $K_i$ and $IC_{50}$ for FIV protease, 0.125 μg of the enzyme was added to a solution (100 μL final volume) containing inhibitor, 560 μM peptide substrate (sequence Gly-Lys-Glu-Glu-Gly-Pro-Pro-Gln-Ala-Tyr-Pro-Ile-Gln-Thr-Val-Asn-Gly (SEQ ID NO: 4)) and 2% dimethyl sulfoxide in a 1:3 mixture of assay buffer (as above) and 4M $NaCl_{aq.}$ solution. The solution was mixed and incubated for 10 minutes at 37° C. and the reaction quenched by addition of 8M guanidine HCl solution containing 0.2 M sodium acetate at pH 4.2 (100 μL). The cleavage products and substrate were separated by reverse phase HPLC. Absorbance was measured at 215 nm, peak areas were determined and percent conversion to product was calculated using relative peak areas. The data were plotted as 1/V (V =rate substrate is cleaved in nmol/min) against inhibitor concentration and the $-K_i$ determined as the point at which the resulting line intersects with $1/V_{max}$ ($Vx_{max}$=6.85 nmol/min). $IC_{50}$ was determined as the inhibitor concentration at 50% inhibition. $V_{max}$ (6.85±0.7 nmol $min^{-1}$) and $K_m$ (707±70 μM) for FIV protease were determined from a plot of 1/V (V=rate in nmol/min) against 1/[S] ([S]=substrate concentration in nmol). The data used was generated similarly to that for $K_i$ with the following modifications. The substrate concentrations used were 560, 448, 336, 224, 111 and 56 μM, in the absence of inhibitor.

Purification of FIV protease:

A 503 base pair Eco R1-Bam H1 fragment containing the coding sequence of FIV protease was cloned from FIV-34TF10 (Talbott et. al. Proc. Natl. Acad. Sci. USA 86 1989, 5743) into the pT7-7 vector (Tabor et. al. Proc. Natl. Acad. Sci USA 82 1985, 1074). The 5' end of the insert was modified by the addition of an Nde1 adaptor, which provided the proper reading frame with initiation of translation from the methionine encoded in the latter site. Translation resulted in production of an 18.6 kDa precursor, which auto-processed to a 13.2 kDa FIV PR plus N- and C-terminal fragments of 3.6 kDa and 1.8 kDa, respectively. The construct was transformed into *E. coli* strain BL21.DE3, lys S (Studier et. al. Meth. Enzymol. 1990, 185, 60) and overnight cultures were used to inoculate 15 liter fermentations, performed using Circlegrow medium (Bio 101) plus 100 μL ampicillin, 20 μM chloramphenicol, at 37° C. The cells were allowed to reach mid-log phase, then the temperature was reduced to 24° C. and IPTG (isopropylβ-thiogalactopyranoside) was added to a final concentration of 1 mM. The fermentation was allowed to proceed for 16 hours, at which time the cells were harvested by centrifugation and frozen at −70° C. in 100 g aliquots for future use.

Cells (100 g) were lysed by addition of 600 mL, 50 mM Tris-HCl, pH 8, 5 mM EDTA and 2 mM 2-mercaptoethanol to the frozen pellet. The cells lysed upon thawing and the viscous mixture was homogenized at 4° C. for 2 min in a Waring blender. The sample was centrifuged at 8,000×g for 20 min and the pellet discarded. The sample was diluted to 1 liter, then subjected to tangential flow against a 300 K cut-off membrane (Filtron) and the PR was washed through the membrane using five liters of the same buffer. The retentate was discarded and the flow-through supernatant concentrated by tangential flow against a 10 K cut-off membrane. The retentate was passed over a DE52 anion exchange column (5×20 cm) equilibrated in the same buffer. The flow-through from this column was passed over an S-Sepharose Fast Flow matrix (2.5×20 cm column, Pharmacia), again equilibrated at pH 8 in the same buffer. The flow-through from S-Sepharose was made 1M with respect to ammonium sulfate and applied to a phenyl sepharose column (Pharmacia, 1.5×10 cm), washed with lysis buffer containing 1M ammonium sulfate, then eluted with a 100–0% linear ammonium sulfate gradient. Peak fractions containing PR were pooled, concentrated using Centripreps (Amicon), and dialyzed against 10 mM Tris-HCl, pH 8, 5 mM EDTA, 2 mM 2-mercaptoethanol. The sample was made 10 mM with respect to MOPS, adjusted to pH 5.5 with HCl, then applied to a Resource S column (Pharmacia) equilibrated in 10 mM Tris-MOPS, pH 5.5, 5 mM EDTA and 2 mM 2-mercaptoethanol. PR was eluted using a linear 0–300 mM NaCl gradient in the same buffer. Peak fractions were pooled, concentrated, and stored as aliquots at −20° C. for further studies. The integrity of the isolated FIV PR was confirmed by ion spray mass spectrometry.

2) Chemical Synthesis

All manipulations were conducted under an inert atmosphere (argon or nitrogen). All solvents were reagent grade. Anhydrous ether, tetrahydrofuran (THF), and toluene were distilled from sodium and/or benzophenone ketyl. Dichloromethane ($CH_2Cl_2$) was distilled from calcium hydride ($CaH_2$). N,N, Dimethylformamide (DMF) and acetonitrile were distilled from phosphorous pentoxide and calcium hydride. Methanol was distilled from magnesium and iodine. Organic acids and bases were reagent grade. All other reagents were commercial compounds of the highest purity available. Analytical thin-layer chromatography (TLC) was performed on Merck silica gel (60 F-254) plates (0.25 mm). Visualization was effected using standard procedures unless otherwise stated. Flash column chromatography was carried out on Merck silica gel 60 particle size (0.040–0.063 mm, 230–400 Mesh). Melting points were determined with a Thomas-Hoover capillary melting point apparatus and are uncorrected. Proton and carbon magnetic resonance spectra ($^1H$-NMR, $^{13}C$-NMR) were recorded on either a Bruker AM-500, AMX-400 or AC250 MHz Fourier transform spectrometer. Coupling constants (J) are reported in hertz and chemical shifts are reported in parts per million (d) relative to tetramethylsilane (TMS, 0 ppm), MeOH (3.30 ppm for $^1H$ and 49.0 ppm for $^{13}C$) or $CHCl_3$ (7.24 ppm for $^1H$ and 77.0 ppm for $^{13}C$) as internal reference. Infrared spectra (IR) were recorded on a Perkin-Elmer 1600 series FT-IR spectrophotometer. Absorptions are reported in wavenumbers ($cm^{-1}$).

Peptide fragments described herein were synthesized using traditional peptide coupling methodologies [EDC (1-(3-dimethylaminopropyl)-3-ethylcarbodiimide HCl), HOBt (1-hydroxybenzotriazole) and DIEA (diisopropylethylamine)]. Esters were hydrolyzed either by base (LiOH for methyl esters) or acid (TFA for $^t$-butyl esters).

Figure 8:
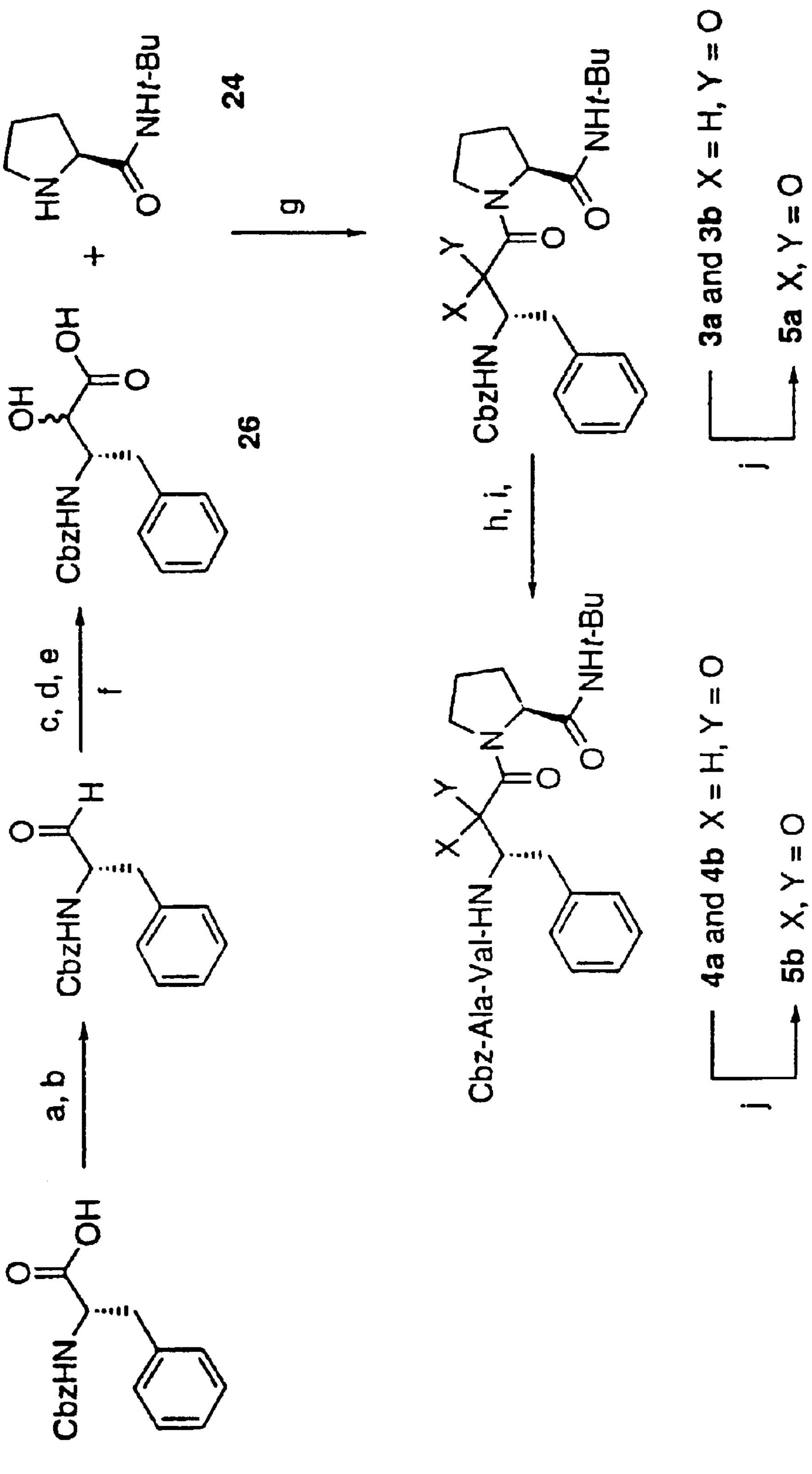
FIG. 8 shows the synthesis of the α-Ketoamides 5a and 5b with the following conditions: (a) $BH_3$, THF. (b) Swern Oxidation (90%). (c) $NaHSO_3$, $H_2O$. (d) KCN. (e) HCl (6N in dioxane), (f) Cbz-Cl, NaOH, $H_2O$ (52%, 4 steps). (g) HBTU, $Et_3N$, $CH_3CN$ (73%). (h) Pd/C, $H_2$, EtOAc. (i) Cbz-Ala-Val-OH, HBTU, $Et_3N$, CH3CN (65%, 2 steps). (j) Dess-Martin (63%).

General Procedure for Coupling Reaction (steps c and d, FIG. 6; step h, FIG. 7; step i, FIG. 8; and step c, FIG. 9).

To a solution of free amine (1.0 mol equiv. as shown in Figure and either purchased from Aldrich, Sigma, Nova Biochem, or Bachem or synthesized herein) and carboxylic acid (1.0 mol equiv. as shown in Figure and either purchased from Aldrich, Sigma, Nova Biochem, or Bachem or synthesized herein) in dry $CH_3CN$ (0.1–0.15 M) was added HBTU (1.0 mol equiv.; Aldrich) followed by $Et_3N$ (1.0 mol equiv. Aldrich) at 20° C. under Argon atmosphere. The reaction mixture was stirred for 15 min then quenched by addition of brine and extracted with EtOAc. The organic layer was then washed sequentially with 1N HCl, sat. aq. $NaHCO_3$, and brine, dried over $MgSO_4$, filtered and concentrated in vacuo. The crude product was purified by flash chromatography to give a desire product.

Standard workup procedure: the reaction mixture being stirred for 15 min then quenched by addition of brine and extracted with EtOAc. Next, the organic layer was then washed sequentially with 1N HCl or saturated ammonium chloride solution (or combination thereof—normality only approximate), sat. aq. $NaHCO_3$, and brine, dried over $MgSO_4$, filtered and concentrated in vacuo. The crude product was purified by flash chromatography to give a desire product.

Standard Dess Martin Oxidation:

As illustrated in FIG. 8, step j, the substrate 3a, 3b, 4a, or 4b (21 mg, 0.044 mmol) was dissolved in dry $CH_2Cl_2$ (2 mL), and Dess-Martin periodinane (26 mg, 0.088 mmol) added. The reaction mixture was stirred at ambient temperature for 24 hours, then diluted with ethyl acetate (10 mL) and quenched by addition of saturated sodium bicarbonate$_{(aq.)}$ (5 mL) and sodium thiosulfate. The aqueous phase was extracted with ethyl acetate (3×20 mL). The combined organic extracts washed with water (10 mL), brine (10 mL), dried ($MgSO_4$) and concentrated in vacuo to give the crude product. Flash chromatography eluting with 30% ethyl acetate in hexane gave the desired product as a 3:1 mixture of diastereomers (colorless oil).

Preferred synthesis of compound 15 as illustrated in FIG. 6.

To a solution of 1,4-bis[(N-Cbz)amino]-1,4-diisobutyl-2,3-diol 14 (450 mg, 0.90 mmol) in 2,2-dimethoxypropane (24 ml) was added catalytic amounts of p-TsOH. The reaction mixture was heated at 600 C. for 5 hr and cooled to 200 C. The reaction mixture was diluted with EtOAc (200 ml), and the resulting solution was washed with sat. aq. NaHCO3 and sat. aq. NaCl, dried over MgSO4, filtered and concentrated in vacuo. The residue was then purified by flash chromatography to give 2,3-protected (1S,2R,3R,4S)-diastereomer 15 (467 g, 96%) as a white solid: 1H NMR (400 MHz, DMSO-$d_6$, 80° C.) d_ 0.80–0.87 (6H, m), 1.11–1.20 (1H, m), 1.27 (3H, s), 1.42–1.49 (1H, m), 1.53–1.61 (1H, m), 3.58 (1H, s), 3.72–3.83 (1H, m), 5.00 (1H, d, J=12.8 Hz), 5.08 (1H, d, J=12.8 Hz), 6.42 (1H, br s), 7.26–7.32 (5H, m); 13C NMR (100 MHz, DMSO-d6, 80° C.) δ 21.1, 22.3, 23.8, 26.4, 41.0, 48.1, 64.8, 78.9, 126.8, 127.0, 127.6, 136.7, 153.4; HRMS (FAB+), calcd for MCs+ C31H44N2O6Cs m/e 673.2254, found m/e 673.2228.

Synthesis of compound 17 as illustrated in FIG. 6.

Compound 15 (480 mg, 0.89 mmol) in EtOAc (30 ml) containing 10% Pd/C (170 mg) was stirred under H2 (1 atm) at 20° C. for 20 hr. The reaction mixture was filtered through Celite and then concentrated in vacuo to give diamine 16 (226 mg, 93%) as a colorless oil, which was used for coupling reaction without purification. To a solution of diamine 16 (194 mg, 0.71 mmol) and N-Cbz-L-Valine (377 mg, 1.50 mmol) in CH3CN (8 ml) was added HBTU (569 mg, 1.50 mmol) followed by Et3N (166 mg, 1.64 mmol). The reaction mixture was stirred for 15 min at 20° C. under Ar then quenched by addition of brine (20 ml) and extracted with EtOAc (4×20 ml). The organic layer was washed sequentially with 1M HCl (5 ml), sat. aq. NaHCO3 (5 ml), and sat. aq. NaCl (5 ml), dried over MgSO4, filtered and concentrated in vacuo. The crude product was purified by flash chromatography to give compound 17 (430 mg, 82%) as a white solid: 1H NMR (400 MHz, DMSO-d6, 25° C.) δ 0.78–0.88 (12H, m), 1.05–1.15 (1H, m), 1.22 (3H, s), 1.47–1.63 (2H, m), 2.01 (1H, q, J=6.4 Hz), 3.42 (1H, s), 3.97 (1H, dd, J=9.0, 6.2), 4.02–4.10 (1H, m), 5.01 (2H, dd, J=17.3, 12.6 Hz), 7.27–7.41 (7H, m); 13C NMR (100 MHz, DMSO-d6, 20° C.) d_ 17.6, 19.3, 21.4, 23.9, 27.0, 30.1, 41.7, 44.5, 60.2, 65.4, 79.2, 107.3, 127.6, 127.7, 128.3, 136.8, 156.0, 171.1; HRMS (FAB+), calcd for MCs+ C41H62N4O8BCs m/e 871.3622, found m/e 871.3648.

Synthesis of compound 19 as illustrated in FIG. 6:

Compound 17 (170 mg, 0.23 mmol) was hydrogenated with 10% Pd/C (50 mg) in EtOAc (8 ml) to give compound 18 (106 mg, 99%) as a colorless viscous oil. It was used for coupling reaction without purification. Next, compound 18 (20 mg, 0.043 mmol) was coupled with N-Cbz-Ala (20 mg, 0.089 mmol) to give compound 19 (28 mg, 75%) as a white solid.

Preferred Synthesis of compound 20 as shown in FIG. 6:

To a solution of compound 19 (25 mg, 0.030 mmol) in MeOH (1.5 ml) was added catalytic amounts of p-TsOH. The reaction mixture was heated at 60° C. for 24 hr then diluted with EtOAc (10 ml). The organic solution was washed with sat. aq. NaHCO3 (2 ml) and sat. aq. NaCl (2 ml), dried over MgSO4, filtered and concentrated in vacuo to give free diol 18 (14 mg, 57%) as a white solid.

The preparations of compound 9–13 were carried out using the general procedures for coupling and deprotection. In a same manner, compound 18 (19 mg, 0.041 mmol) was coupled to N-Cbz-Leu (23 mg, 0.086 mmol) to give compound 20 (23 mg, 58%) as a white solid.

Preferred synthesis of compound 21 as illustrated in FIG. 6.

Compound 18 (22 mg, 0.047 mmol) was coupled to N-Cbz-Phe (30 mg, 0.098 mmol) to give compound 21 (30 mg, 63%) as a white solid: 1H NMR (500 MHz, DMSO-d6, 80° C.) δ 0.76–0.92 (12H, m), 1.15–1.20 (1H, m), 1.29 (3H, s), 1.45–1.60 (2H, m), 1.98–2.10 (1H, m), 2.78–2.85 (1H, m) 3.51 (1H, s), 4.08–4.15 (1H, br), 4.25–4.35 (2H, m), 4.95 (2H s), 7.12–7.35 (12H, m), 7.56 (1H, d, J=8.5 Hz); HRMS (FAB+), calcd for MCs+ C59H80N6O10Cs m/e 1165.4990, found m/e 1165.4936.

Preferred synthesis of compound 10 as illustrated in FIG. 6.

Compound 21 (20 mg, 0.019) was deprotected to give compound 10 (11 mg, 58%) as a white solid: 1H NMR (400 MHz, DMSO-d6, 80° C.) δ 0.83–0.89 (12H, m), 1.18–1.25 (1H, m), 1.43–1.58 (2H, m), 2.02 (1H, q, J=6.7 Hz), 2.82 (1H, dd, J=14.1, 9.8 Hz), 3.04 (1H, dd, J=14.2, 4.4 Hz), 3.23 (1H, s), 4.10–4.20 (2H, m), 4.32–4.38 (1H, m), 4.95 (2H, s), 6.95–7.00 (2H, m), 7.15–7.32 (10H, m), 7.54 (1H, d, J=8.5 Hz); 13C NMR (100 MHz, DMSO-d6, 25 ∞_C) d_ 17.3, 18.7, 21.5, 22.6, 23.6, 29.7, 37.0, 41.5, 47.3, 55.7, 57.7, 64.9, 72.5, 125.5, 126.7, 127.0, 127.3, 127.6, 128.5, 137.4, 139.1, 156.0, 169.6, 170.6; HRMS (FAB+), calcd for MCs+ C56H76N6O10Cs m/e 1125.4677, found m/e 1125.4709.

Preferred synthesis of compound 22 as illustrated in FIG. 6.

Compound 18 (22 mg, 0.047 mmol) was coupled to N-Cbz-Val (25 mg, 0.098 mmol) to give compound 22 (31 mg, 70%) as a white solid: 1H NMR (500 MHz, DMSO-d6, 80° C.) δ 0.75–0.88 (18H, m), 1.12–1.19 (1H, m), 1.28 (3H, s), 1.45–1.60 (2H, m), 2.00 (2H, br s), 3.50 (1H, s), 3.92–3.99 (1H, m), 4.03–4.12 (1H, br s), 4.25–4.32 (1H, m), 4.98–5.08 (2H m), 6.89–6.95 (1H, br), 7.25–7.38 (6H, m), 7.48 (1H, d, J=8.9 Hz); HRMS (FAB+), calcd for MCs+ C51H80N6O10Cs m/e 1069.4990, found m/e 1069.4943. Compound 22 (24 mg, 0.025) was deprotected to give compound 11(11 mg, 50%) as a white solid: 1H NMR (400 MHz, DMSO-d6, 80 ∞_C) d_ 0.80–0.88 (18H, m), 1.13–1.22 (1H, m), 1.41–1.56 (2H, m), 1.95–2.04 (2H, m), 3.20 (1H, s), 3.94 (1H, dd, J=8.9, 6.6 Hz), 4.11 (1H, se, J=4.4 Hz), 4.17 (1H, dd, J=8.8, 6.6 Hz), 5.04 (2H, s), 6.74 (1H, d, J=8.2 Hz), 6.94 (1H, d, J=9.3 Hz), 7.25–7.35 (5H, m), 7.43 (1H, d, J=8.8 Hz); 13C NMR (100 MHz, DMSO-d6, 80° C.) δ 17.3, 18.5, 18.7, 21.5, 22.6, 23.6, 29.6, 29.7, 41.5, 47.3, 57.6, 60.0, 65.0, 72.5, 126.9, 127.0, 127.6, 137.4, 156.0, 169.7, 170.3; HRMS (FAB+), calcd for MCs+ C48H76N6O10Cs m/e 1029.4677, found m/e 1029.4701.

Preferred synthesis of compound 12 as illustrated in FIG. 6.

(1S,2R,3R,4S)-1,4-bis[(N-Cbz)amino]-1,4-dibenzyl-2,3-diol derivative 23 was prepared by applying the procedure described (Lee et al. Proc. Natl. Acad. Sci. USA 1998, 95, 939–944). Compound 23 (40 mg, 0.074 mmol) was coupled to N-Cbz-Ser (38 mg, 0.16 mmol) to give the adduct (60 mg, 83%) as a white solid: (500 MHz, DMSO-d6, 80° C.) δ 0.66 (3H, d, J=6.5), 0.72 (3H, d, J=6.0), 1.31 (3H, s), 1.90 (1H, d, J=6.2 Hz), 2.65–2.80 (2H, m), 3.13–3.17 (1H, m), 3.58 (2H, s), 4.07–4.16 (2H, m), 4.23–4.31 (1H, m), 4.60–4.70 (1H, m), 5.05 (2H, s), 6.90–6.99 (1H, br), 7.07–7.19 (6H, m), 7.25–7.35 (5H, m), 7.45–7.50 (1H, br); HRMS (FAB+), calcd for MCs+ C53H68N6O12Cs m/e 1113.3990, found m/e 1113.3897. The adduct (30 mg, 0.031 mmol) was then deprotected as above to give compound 12 (15 mg, 51%) as a white solid: 1H NMR (400 MHz, DMSO-d6, 80° C.) δ 0.70 (3H, d, J=6.5 Hz), 0.72 (3H, d, J=7.0 Hz), 1.91 (1H, se, J=6.5), 2.68–2.82 (2H, m), 3.33 (1H, s), 3.60–3.65 (2H, m), 4.07 (1H, dd, J=9.0, 6.5 Hz), 4.16 (1H, q, J=8.0), 4.29 (1H, s), 4.37–4.43 (1H, m), 4.63–4.70 (1H, m), 5.07 (2H, s), 6.82–6.92 (1H, br), 7.05–7.40 (12H, m); 13C NMR (100 MHz, DMSO-d6, 80° C.) δ 17.6, 19.3, 30.3, 38.5, 50.5, 57.0, 57.8, 61.8, 65.5, 73.2, 125.7, 127.8, 128.4, 129.1, 136.9, 139.0, 155.9, 169.9, 170.2; HRMS (FAB+), calcd for MCs+ C50H64N6O12Cs m/e 1073.3637, found m/e 1073.3685.

Preferred synthesis of compound 13 as described in FIG. 6.

Compound 23 (33 mg, 0.061 mmol) was coupled to N-Cbz-Thr (33 mg, 0.13 mmol) to give the adduct (52 mg, 85%) as a white solid: (500 MHz, DMSO-d6, 80° C.) δ 0.69 (3H, d, J=7.0 Hz), 0.74 (3H, d, J=6.5 Hz), 1.03 (3H, d, J=6.5 Hz), 1.32 (3H, s), 1.93 (1H, se, J=6.0 Hz), 2.68–2.80 (2H, m), 3.60 (1H, s), 3.90–3.98 (1H, m), 4.02 (1H, dd, J=8.5, 5.0), 4.20 (1H, dd, J=8.5, 6.0 Hz), 4.27–4.32 (1H, m), 4.56 (1H, d, J=5.5 Hz), 5.06 (2H, s), 6.65–6.75 (1H, br), 7.10–7.19 (6H, m), 7.28–7.35 (5H, m), 7.44 (1H, d, J=9.0 Hz); HRMS (FAB+), calcd for MCs+ C55H72N6O12Cs m/e 1141.4263, found m/e 1141.4316. The adduct (35 mg, 0.037 mmol) was then deprotected to give compound 13 (20 mg, 56%) as a white solid: 1H NMR (500 MHz, DMSO-d6, 80° C.) δ 0.69 (3H, d, J=6.5 Hz), 0.72 (3H, d, J=7.0 Hz), 1.04 (3H, d, J=6.5 Hz), 1.87–1.93 (1H, m), 2.68–2.80 (2H, m), 3.33 (1H, s), 3.90–4.15 (3H, m), 4.22–4.38 (2H, m), 5.06 (2H, s), 6.60–6.70 (1H, br), 7.05–7.40 (11H, m), 7.50 (1H, d, J=8.0 Hz); 13C NMR (100 MHz, DMSO-d6, 20° C.) δ 17.6, 19.3, 19.7, 30.6, 38.5, 50.6, 57.5, 60.3, 65.5, 66.8, 73.1, 125.5, 127.7, 127.8, 128.0, 128.4, 129.0, 136.9, 138.9, 156.0, 169.7, 170.2; HRMS (FAB+), calcd for MCs+ C52H68N6O12Cs m/e 1101.3950, found m/e 1101.3900.

Synthesis of compound 14 and compound 23 as shown in FIG. 6

The key intermediates (1S,2R,3R,4S)-1,4-bist[(N-Cbz) amino]-1,4-dibenzyl-2,3-diol (used for preparation of compound 23) and (1S,2R,3R,4S)-1,4-bis[(N-Cbz)amino]-1,4-diisobutyl-2,3-diol 14 were prepared by the stereoselective Pinacol coupling of L-Cbz-phenylalanal (for 23) or L-Cbz-leucinal (for 14) (Each from Aldrich or Sigma), respectively. Using conditions exactly as described in Konradi, A. W.; Pedersen, S. F. J. Org. Chem. 1992, 57, 28–32. Compound 14 was carried onto the next step. Compound 23 was formed by reacting the formed diol intermediate with 0.10 equiv. p-TsOH in 1.0 Molar 2,2-dimethoxypropane at 25° C. for 1 hour until complete, followed by standard workup and purification conditions.

Synthesis of compounds 8, 9, 10 and 11 as shown in FIG. 6.

Compound 14 was reacted with 1.0 Molar 2,2-dimethoxypropane with 0.10 equiv. p-TsOH (80%) at 25° C. for 1 hour until complete, followed by standard workup and purification conditions as described herein to form 15; (b) Intermediate 15 from step a was suspended in 0.10 M MeOH at 25° C. and catalytic amount of 10% Pd/C was added under $H_2$ balloon and stirred for 1 hour or until complete, followed by standard workup and purification conditions. (99%) to form 16; (c) General Procedure for Coupling Reaction using HBTU, Cbz-Val, Et3N, $CH_3CN$ (89%), followed by standard workup and purification conditions to form 17; Intermediate 17 was suspended in 0.10 M MeOH at 25° C. and catalytic amount of 10% Pd/C was added under $H_2$ balloon and stirred for 1 hour or until complete, followed by standard workup and purification conditions. (99%) to form 18 (d) General Procedure for Coupling Reaction as described above using Intermediate 18, HBTU, Cbz-amino acids (Aldrich, Sigma, Nova Biochem, or Bachem), $Et_3N$, $CH_3CN$, followed by standard workup and purification conditions to form intermediate (depending on amino acid used to form 19–22); (e) Intermediate (either 19–22) was finally suspended in a cataltyic amount of p-TsOH (0.10 equiv.) in 0.10 M MeOM at 25° C. for 1 hour until complete, followed by standard workup and purification conditions to seperately form 8, 9, 10, or 11.

Synthesis of compounds 12 or 13 as shown in FIG. 6

General Procedure for Coupling Reaction as described above using Intermediate 23, HBTU, Cbz-amino acids (Aldrich, Sigma, Nova Biochem, or Bachem), $Et_3N$, $CH_3CN$, followed by standard workup and purification conditions to form intermediate (depending on amino acid used to form intermediate); (e) Intermediate was finally suspended in a cataltyic amount of p-TsOH (0.10 equiv.) in 0.10 M MeOH at 25° C. for 1 hour until complete, followed by standard workup and purification conditions to seperately form 12 or 13.

Synthesis of compound 25 as shown in FIG. 7:

Compound 25 was formed from the multi step process as shown in FIG. 7 (with all intermediates purified by silica gel chromatography). Step (a) Free acid 1.0 equiv. (Aldrich), NMM 1.1 equiv. (Aldrich), 0.10 M THF, 1.1 equiv. i-BuOCOCl were mixed together for 1 hour at 0° C. until complete by TLC monitoring, the reaction was next quenched via standard workup as described above and carried on to the next step after column chromatography. Step (b) 1.0 equiv. of intermediate compound from step a was suspended in solution with 1.1 equiv. $CH_2N_2$ (diazomethane formed by standard methods—see March, Carey and Sundburg, Caruthers or any advanced organic text for standard procedure of generating diazomethane), 0.10 M $Et_2O$, mixed together for 1 hour at 0° C. until complete by TLC monitoring, the reaction was next quenched via standard workup as described above and carried on to the next step after column chromatography. Step (c) 1.0 equiv. of intermediate compound from step b was suspended in solution with 0.01 M HCl/0.10 M THF, mixed together for 1 hour at 0° C. until complete by TLC monitoring, the reaction was next quenched via standard workup as described above and carried on to the next step after column chromatography (85%, for the 3 above steps from step a–c). Step (d) 1.0 equiv. of intermediate compound from step c was suspended in solution with 1.1 equiv. $NaBH_4$ (1.0 M/THF added dropwise at 0° C.), 0.10 M EtOH, (90% d.e, 81%) mixed together for 1 hour at 0° C. until complete by TLC monitoring, the reaction was next quenched via standard workup as described above and carried on to the next step after column chromatography. Step (e) 1.0 equiv. of intermediate compound from step d was suspended in solution with 10 equiv. NaOMe, 1.0 M MeOH, 25° C. for 1 hour until complete by TLC monitoring, the reaction was next quenched via standard workup as described above and carried on to the next step after column chromatography (96%) to form compound 25.

Synthesis of compound 2b as shown in FIG. 7:

Compound 25 (18 mg, 0.039 mmol in 0.10 M MeOH, 1.1 equiv. $Et_3N$ was added 1.1 equiv. 24 (Slee et al. ibid; Aldrich/Sigma) to 25; stir 0.0° C. until complete by TLC, standard workup/chromatography (90%)) and prepared exactly as conditions described in Slee et al. J. Am. Chem. Soc. 1995, 117, 11867–11878). The intermediate was then hydrogenated with 10% Pd/C (15 mg) in EtOAc (2 ml) to give an amine 2a as a colorless oil (standard reduction conditions as described above) filtration of Pd/C from solution then condensation of EtOAc and carry onto next step. The General Procedure for Coupling Reaction as described above, was next used with the crude amine 2a, Cbz-Ala-Val-OH (12 mg, 0.039 mmol; Aldrich/Sigma, Nova Biochem, or Bachem), HBTU (14 mg, 0.038 mmol) and Et3N (4.7 mg, 0.046 mmol) in $CH_3CN$ (1 ml) and gave compound 2b (12 mg, 49%) as a white solid: $^1H$ NMR (500 MHz, DMSO-$d_6$, 60° C.) δ0.76 (6H, d, J=6.7 Hz), 1.20 (3H, d, J=7.1 Hz), 1.26 (9H, s), 1.64–1.70 (3H, br), 1.86–1.90 (1H, m), 1.98–2.00 (1H, m), 2.67 (1H, m), 2.69 (1H, m), 2.93 (1H, b), 2.96 (1H, b), 3.03 (3H, m), 3.50 (1H, b), 4.00–4.13 (3H, m), 5.04 (2H, s), 7.10–7.50 (14H, m); 13C NMR (100 MHz, DMSO-d6, 60° C.) d_ 18.0, 19.2, 28.3, 30.0, 30.8, 34.7, 38.2, 49.5, 50.1, 52.8, 55.5, 57.7, 59.4, 65.3, 67.8, 71.0, 125.7, 127.6, 127.7, 127.8, 128.3, 129.2, 137.0, 138.8, 155.6, 170.2, 170.3, 172.0; HRMS (FAB+), calcd for MCs+ C35H51N5O6Cs m/e 770.2894, found m/e 770.2922.

Synthesis of aldhehyde as shown in FIG. 8:

To 1.0 equivalents of acid (Aldrich/Sigma) is added 1.1 equiv. of a 1.0 Molar solution of $BH_3$ (THF soln) in 0.10 Molar THF total reaction solution mixed together for 1 hour at 0° C. until complete by TLC monitoring, the reaction was next quenched via standard workup as described above and carried on to the next step after column chromatography. (b) Intermediate from step a is exposed to standard Swern Oxidation conditions well known in the art using standard amounts of oxalyl chloride/triethyl amine in methylene chloride and mixed together for 1 hour at 0° C. until complete by TLC monitoring, the reaction was next quenched via standard workup as described above and carried on to the next step after column chromatography. (90%).

Synthesis of α-hydroxy-acid compound 26 as shown in FIG. 8:

Above synthesized intermediate aldehyde (1.0 equivalents) was suspended with 1.1 equiv. $NaHSO_3$ in 1.0 THF/$H_2O$ combination mixed together for 1 hour at 0° C. until complete by TLC monitoring, the reaction was next quenched via standard workup as described above and carried on to the next step after column chromatography. (d) Above synthesized intermediate (1.0 equivalents) was suspended with 1.1 equiv KCN in 1.0 Molar acetonitrile mixed together for 1 hour at 0° C. until complete by TLC monitoring, the reaction was next quenched via standard workup as described above and carried on to the next step after column chromatography. (e) Above synthesized intermediate (1.0 equivalents) was next suspended with 1.1 equiv HCl in 6N in dioxane mixed together for 1 hour at 0° C. until complete by TLC monitoring, the reaction was next quenched via standard workup as described above and carried on to the next step after column chromatography. (f) Finally synthesized intermediate (1.0 equivalents) was suspended with Cbz-Cl (Aldrich), 1.0 Molar solution of 1.1 equiv. NaOH in 0.01 Molar THF/$H_2O$ mixed together for 1 hour at 0° C. until complete by TLC monitoring, the reaction was next quenched via standard workup as described above and carried on to the next step after column chromatography (52%, 4 steps).

Synthesis of compound 3a as shown in FIG. 8:

(g) HBTU, $Et_3N$, $CH_3CN$ (73%); pyrolidine amine from Aldrich/Sigma and coupling was achieved using exactly the protocol described herein for general peptide coupling conditions.

Synthesis of compound 3b as shown in FIG. 8:

A mixture of diastereomer 3a (85 mg, 0.170 mmol) was hydrogenated with 10% Pd/C (20 mg) in EtOAc (3 ml) to give an amine as a colorless oil. The crude amine, Cbz-Ala-Val-OH, (55 mg, 0.170 mmol), HBTU (65 mg, 0.170 mmol) and Et3N (20 mg, 0.20 mmol) in CH3CN (4 ml) gave separable mixture of compounds 3b and 4b (72 mg, 65%) as a white solid; Compound 3b: 1H NMR (400 MHz, CD3OD, 20 ∞C) d__0.82 (6H, br s), 1.28–1.33 (12H, m), 1.80–2.05 (5H, m), 2.80–2.97 (4H, m), 3.36 (1H, br), 4.10–4.20 (2H, m), 4.25 (1H, br s), 4.44 (1H, br s), 5.09 (2H, s), 7.20 (1H, br), 7.24–7.55 (13H, m); 13C NMR (100 MHz, CD3OD, 20° C.) δ 18.0, 18.3, 19.9, 25.5, 28.8, 30.7, 32.1, 38.8, 47.8, 52.0, 52.9, 60.1, 62.3, 67.7, 70.4, 127.7, 128.9, 129.0, 129.5, 129.6, 130.5, 139.4, 158.1, 172.0, 172.7, 173.8; HRMS (FAB+), calcd for MCs+ C35H51N5O6Cs m/e 770.2894, found m/e 770.2922.

Synthesis of compound 4b as shown in FIG. 9:

A mixture of diastereomer 3a (85 mg, 0.170 mmol) was hydrogenated with 10% Pd/C (20 mg) in EtOAc (3 ml) to give an amine as a colorless oil. The crude amine, Cbz-Ala-Val-OH (55 mg, 0.170 mmol), HBTU (65 mg, 0.170 mmol) and Et3N (20 mg, 0.20 mmol) in CH3CN (4 ml) gave separable mixture of compounds 3b and 4b (72 mg, 65%) as a white solid; Compound 4b: 1H NMR (400 MHz, DMSO-d6, 60° C.) δ_ 0.74–0.77 (6H, m), 1.21–1.23 (3H, overlapping), 1.23 (9H, s), 1.81–1.91 (5H, b), 2.70 (1H, m), 2.71 (1H, m), 2.78 (1H, b), 2.89 (1H, b), 3.00 (1H, b), 3.36–3.41 (4H, m), 5.04 (2H, s), 7.16–7.44 (14H, m); 13C NMR (100 MHz, DMSO-d6 , 60° C.) d__17.1, 17.6, 18.7, 23.3, 28.1, 30.1, 36.8, 37.8, 45.7, 49.6, 50.0, 57.3, 60.1, 65.1, 69.4, 125.6, 127.1, 127.2, 127.6, 127.8, 128.6, 136.6, 138.2, 155.1, 169.9, 171.6; HRMS (FAB+), calcd for MCs+ C35H51N5O6Cs m/e 770.2894, found m/e 770.2947.

Synthesis of compound 5a as illustrated in FIG. 8:

Dess-Martin reagent (22 mg, 0.074 mmol) was added to a solution of diasteromer 3b (16 mg, 0.025 mmol; as described above and in Slee et al., ibid) in methylene chloride (2 ml). The reaction mixture was stirred for 12 hrs then quenched by addition of brine and extracted with EtOAc. The organic layer was then washed with sat. aq. NaHCO3, and brine, dried over MgSO4, filtered and concentrated in vacuo. The crude product was purified by flash chromatography to give compound 5a (10 mg, 63%) as a mixture of isomers (1:1):

Synthesis of compound 5b as illustrated in FIG. 8:

Dess-Martin reagent (22 mg, 0.074 mmol; procedure described above) was added to a solution of diasteromer 3b and 4b (16 mg, 0.025 mmol) in CH2Cl2 (2 ml). The reaction mixture was stirred for 12 hrs then quenched by addition of brine and extracted with EtOAc. The organic layer was then washed with sat. aq. NaHCO3, and brine, dried over MgSO4, filtered and concentrated in vacuo. The crude product was purified by flash chromatography to give compound 5b (10 mg, 63%) as a mixture of isomers (1:1): 1H NMR (500 MHz, DMSO-d4, 60° C.) δ0.76–0.85 (6H, m), 1.16, 1.18 (3H, d, J=7.0 Hz), 1.24, 1.26 (9H, s), 1.70–1.80 (3H, m), 1.82–2.08 (3H, m), 2.15–2.22 (1H, m), 2.60 (1H, dd, J=10.5, 14.6 Hz), 2.96 (1H, dd, J=9.1, 14.2 Hz), 3.17 (1H, dd, J=4.9, 14.2), 3.24–3.26 (1H, m), 3.38–3.65 (5H, m), 4.07–4.12 (3H, m), 4.19 (1H, t, J=6.6 Hz), 4.24 (2H, t, J=5.7 Hz), 4.62 (1H, q, J=4.3 Hz), 4.95–4.99 (1H, m), 5.01 (2H, s), 5.26 (1H, m), 7.15–7.45 (12H, m); 13C NMR (100 MHz, DMSO-d4, 60 ∞C) d__ __17.6, 18.0, 19.1, 21.7, 24.4, 28.4, 29.1, 31.0, 32.4, 33.7, 34.2, 35.6, 47.4, 50.0, 50.2, 55.9, 56.7, 56.8, 57.1, 57.5, 59.8, 60.4, 65.3, 126.2, 126.5, 127.7, 127.7, 128.1, 128.2, 128.3, 128.4, 128.6, 128.9, 137.1, 137.2, 138.0, 140.5, 155.6, 162.0, 162.2, 169.8, 170.7, 171.0, 171.4, 172.1, 172.2, 196.0, 198.1; HRMS (FAB+), calcd for MCs+ C35H47N5O7Cs m/e 782.2530, found m/e 782.2558.

Synthesis of compound 6b as described in FIG. 9:

The amine 6a (20 mg, 0.047 mmol; prepared according to the figure and exactly as described in Kempf et al. J. Med. Chem. 1998, 41, 602–617), Cbz-Ala-Val-OH (15 mg, 0.047 mmol), HBTU (18 mg, 0.047 mmol) and Et3N (5.7 mg, 0.056 mmol) in $CH_3CN$ (1 ml) gave the title compound 6b (25 mg, 73%) as a white solid (see general coupling protocol for exact procedure as described herein): $^1$H NMR (400 MHz, DMSO-d6, 80° C.) δ 0.75–0.78 (6H, m), 1.21 (3H, d, J=7.1 Hz), 1.48–1.56 (2H, m), 1.85–1.94 (1H, m), 2.62–2.79 (3H, m), 3.58 (1H, m), 3.79 (1H, m), 4.05–4.08 (1H, m), 4.10–4.13 (2H, m), 5.04 (2H, d, J=2.5 Hz), 5.14 (2H, s), 7.08–7.34 (15H, m), 7.80 (1H, s), 8.98 (1H, s); 13C NMR (100 MHz, DMSO-d6, 80° C.) δ__ 17.4, 18.7, 30.2, 37.0, 38.0, 46.9, 50.0, 52.9, 55.5, 57.0, 57.5, 65.1, 68.6, 125.3, 127.1, 127.2, 127.4, 127.4, 127.8, 128.5, 128.6, 128.7, 133.5, 136.9, 138.2, 138.8, 142.3, 154.4, 155.0, 169.2, 170.0, 171.5; HRMS (FAB+), calcd for MCs+ C39H47N5O7SCs m/e 862.2277, found m/e 862.2251.

Synthesis of compound 7a as illustrated in FIG. 9:

Compound 7a: The amine of 7 (30 mg, 0.075 mmol; Thompson et al. J. Am. Chem. Soc. 1993, 115, 801–803) prepared from the BOC derivative (Thompson et al, ibid) was coupled with Cbz-Ala-Val-OH (24 mg, 0.075 mmol; Aldrich), using standard coupling conditions (eg. HBTU (28 mg, 0.075 mmol) and $Et_3N$ (9.1 mg, 0.09 mmol) in CH3CN (1 ml)) gave the title compound 7a (40 mg, 76%) as a white solid: $^1$H NMR (500 MHz, DMSO-$d_6$, 80° C.) δ0.73 (3H, d, J=6.8 Hz), 0.75 (3H, d, J=6.8 Hz), 1.19 (3H, d, J=7.08 Hz), 1.26 (9H, s), 1.31–1.43 (4H, b), 1.48 (2H, b), 1.59 (1H, b), 1.63 (1H, b), 1.73 (1H, b), 1.82–1.98 (3H, m), 2.05–2.13 (2H, m), 2.57–2.66 (3H, m), 2.93–2.98 (2H, m), 4.06–4.20 (3H, m), 5.03 (2H, s), 7.09–7.39 (14H, m); 13C NMR (100 MHz, DMSO-d6, 80° C.) δ16.9, 17.8, 18.2, 18.6, 19.3, 20.4, 24.8, 25.9, 28.4, 29.8, 30.6, 31.2, 32.4, 33.3, 35.7, 49.9, 52.1, 57.3, 58.0, 65.3, 69.8, 125.4, 127.6, 127.7, 127.8, 128.3, 129.3, 137.0, 140.2, 155.6, 170.1, 172.0, 172.7; HRMS (FAB+), calcd for MCs+ C40H59N5O6Cs m/e 838.3520, found m/e 838.3546.

Preferred synthesis of compound 7b as illustrated in FIG. 9:

The amine of 7 ((49 mg, 0.122 mmol); Thompson et al. J. Am. Chem. Soc. 1993, 115, 801–803) prepared from the BOC derivative 7, was coupled with Cbz-Ala-Asn-OH (41 mg, 0.122 mmol; Aldrich or as described above), using the standard coupling conditions eg. (HBTU (46 mg, 0.122 mmol) and Et3N (12.4 mg, 0.09 mmol) in DMF (1 ml)) gave the title compound 7b (42 mg, 78%) as a white solid: δ 1.22 (3H, d, J=7.1 Hz), 1.27 (9H, s), 1.31–1.85 (10H, m), 1.90 (2H, m), 2.22 (1H, b), 2.33 (1H, b), 2.49–2.58 (3H, m), 2.71 (1H, dd, J=9.4, 14.3 Hz), 2.81 (1H, m), 2.91–2.94 (1H, m), 3.18–3.25 (2H, m), 3.74 (1H, m), 4.08 (1H, q, J=7.3 Hz), 4.52 (1H, q, J=6.3, Hz), 5.03 (2H, s), 7.13–7.35 (10H, m); 13C NMR (100 MHz, DMSO-d6, 20° C.) δ18.3, 20.2, 21.3, 25.2, 26.0, 28.3, 29.5, 30.5, 32.8, 34.7, 35.6, 37.5, 49.5, 50.1, 50.3, 58.3, 58.5, 61.2, 65.5. 68.0, 126.7, 127.8, 127.9. 128.4, 128.7, 129.6, 137.1, 137.4, 155.7, 158.0, 158.3, 172.1, 173.2; HRMS (FAB+), calcd for MH+ C39H57N6O7 m/e 721.4262, found m/e 721.4289

Synthesis of compound 100 as illustrated in FIG. 12.

1,4-Bis[(N-Cbz)amino]-1,4-dibenzyl-2,3-diol 100 was prepared using literature procedure, Konradi et al. J. Org. Chem., 57, 28–32. All new compounds were homogeneous by TLC and were characterized by satisfactory $_1$H, __C NMR, and mass spectra.

Synthesis of Compound 200 as illustrated in FIG. 12.

To a suspension of diastereomeric mixture of 1.4-bis [(NCbz)amino]-1,4-dibenzyl-2,3-diol 100 (1.5 g, 2.63 mmol) in 2,2-dimethoxypropane (50 ml) was added catalytic amounts of p-TsOH. The reaction mixture was heated at 60° C. for 5 hr and cooled to 20° C. The reaction mixture was diluted with EtOAc (200 ml), and the resulting solution was washed with sat. aq. $NaHCO_3$ and sat. aq. NaCl, dried over $MgSO_4$, filtered and concentrated in vacuo. The residue was then purified by flash chromatography (hexanes/EtOAc 80/20) to give 2,3-protected (1S,2R,3R, 4S)-diastereomer 200 (1.28 g, 80%) as a white solid.

Synthesis of compound 400 as illustrated in FIG. 12 (General Procedure for the Coupling Reaction).

Compound 2 (1.20 g, 1.97 mmol) in EtOAc (75 ml) containing 10% Pd/C (400 mg) was stirred under $H_2$ (latm) at 20° C. for 20 hr. The reaction mixture was filtered through Celite and then concentrated in vacuo to give diamine 300 (664 mg, 99%) as a colorless viscous oil, which was used for coupling reaction without purification.

To a solution of diamine 300 (650 mg, 1.91 mmol) and N-Cbz-L-Valine (961 mg, 3.82 mmol) in $CH_3CN$ (16 ml) was added HBTU (1.45 g, 3.82 mmol) followed by $Et_3N$ (425 mg, 4.2 mmol). The reaction mixture was stirred for 15 min at 20° C. under Ar then quenched by addition of brine (60 ml) and extracted with EtOAc (4×50 ml). The organic layer was washed sequentially with 1M HCl (10 ml), sat. aq. $NaHCO_3$ (10 ml), and sat. aq. NaCl (10 ml), dried over $MgSO_4$, filtered and concentrated in vacuo. The crude product was purified by flash chromatography to give compound 400 (1.16 g, 75%) as a white solid.

Synthesis of compound 1000 as illustrated in FIG. 12 (General Procedure for Deprotection).

To a solution of compound 400 (55 mg, 0.068 mmol) in MeOH (3 ml) was added catalytic amounts of p-TsOH. The reaction mixture was heated at 60° C. for 24 hr then diluted with EtOAc (20 ml). The organic solution was washed with sat. aq. $NaHCO_3$ (5 ml) and sat. aq. NaCl (5 ml), dried over $MgSO_4$, filtered and concentrated in vacuo to give free diol 1000 (36 mg, 69%) as a white solid.

The preparations of compound 1100–1400 were carried out using the general procedures for coupling and deprotection.

Synthesis of compound 1100 as illustrated in FIG. 12.

In a same manner, compound 400 (1.10 g, 1.36 mmol) was hydrogenated to give compound 500 (665 mg, 99%) as a colorless viscous oil.

Compound 500 (20 mg, 0.037 mmol) was coupled to give Compound 600 (27 mg, 79%) as a white solid.

Compound 600 (22 mg, 0.024) was deprotected to yield compound 1100 (13 mg, 62%) as a white solid: $_1$H NMR (400 MHz, DMSO-$d_6$, 80° C.) d 0.74 (3H, d, J=4.9), 0.76

(3H, d, J=4.9), 1.90 (1H, se, J=6.4), 2.72–2.80 (2H, m), 3.37 (1H, s), 3.68–3.73 (3H, m), 4.10 (1H, dd, J=8.3, 6.7), 4.33 (1H, s), 4.36–4.42 (1H, m), 5.09 (2H, s), 7.02–7.09 (1H, br), 7.10–7.41 (12H, m); _C NMR. (100 MHz, DMSO-$d_6$, 80° C.) d 17.1, 19.0, 30.1, 39.0, 42.5, 50.7, 58.0, 65.7, 72.5, 125.5, 125.7, 128.2, 128.5, 128.8, 129.4, 136.6, 138.8, 155.7, 168.5, 170.2; HRMS (FAB+), calcd for MCs+ $C_{48}H_{60}N_6O_{10}Cs$ m/e 1013.3425, found m/e 1013.3447.

Synthesis of compound 1200 as illustrated in FIG. 12.

Compound 500 (68 mg, 0.13 mmol)was converted to compound 700 (80 mg, 67%) as a white solid.

Compound 700 (55 mg, 0.058) was deprotected to give compound 1200 (42 mg, 80%) as a white solid: $_1$H NMR (400 MHz, DMSO-$d_6$, 80° C.) d 0.70 (3H, d, J=2.4), 0.72 (3H, d, J=2.4), 1.21 (3H, d, J=7.0), 1.87 (1H, se, J=6.7), 2.69–2.79 (2H, m), 3.32 (1H, s), 4.03 (1H, dd, J=8.8, 6.4), 4.10 (1H, qu, J=7.0), 4.27 (1H, s), 4.34–4.40 (1H, m), 5.04 (2H, s), 6.92–6.96 (1H, br), 7.05–7.34 (12H, m); _C NMR (100 MHz, DMSO-$d_6$, 80° C.) d 17.3, 17.6, 18.7, 29.7, 38.0, 49.9, 50.4, 57.8, 65.1, 72.5, 125.1, 127.0, 127.2, 127.3, 127.8, 128.6, 136.6, 138.4, 155.1, 169.8, 171.6; HRMS (FAB+), calcd for MCs+ $C_{50}H_{64}N_6O_{10}Cs$ m/e 1041.3738, found m/e 1041.3780.

Synthesis of compound 1300 as illustrated in FIG. 12.

Compound 500 (50 mg, 0.093 mmol) was converted to compound 800 (52 mg, 54%) as a white solid.

Compound 1300 (22 mg, 65%) was prepared from compound 800 (35 mg, 0.034)as a white solid: $_1$H NMR (400 MHz, DMSO-$d_6$, 80° C.) d 0.73 (6H, d, J=6.8), 0.87 (3H, d, J=6.5), 0.89 (3H, d, J=6.5), 1.48 (2H, t, J=6.8), 1.59–1.67 (1H, m), 1.88 (1H, se, J=6.7), 2.70–2.80 (2H, m), 3.34 (1H, s), 4.04–4.93 (2H, m), 4.23 (1H, s), 4.32–4.38 (1H, m), 5.05 (2H, s), 7.02–7.36 (13H, m); _C NMR (100 MHz, DMSO-$d_6$, 80° C.) d 17.2, 18.7, 21.1, 22.3, 23.8, 29.8, 37.9, 40.3, 50.4, 53.2, 57.4, 65.1, 72.2, 125.1, 126.9, 127.1, 127.2, 127.7, 128.5, 136.5, 138.3, 155.3, 169.7, 171.3; HRMS (FAB+), calcd for MCs+ $C_{56}H_{76}N_6O_{10}Cs$ m/e 1125.4677, found m/e 1125.4720.

Synthesis of compound 1400 as illustrated in FIG. 12.

Compound 500 (49 mg, 0.091 mmol) was converted to compound 900 (68 mg, 68%) as a white solid.

Compound 900 (43 mg, 0.039) was then deprotected to give compound 1400 (30 mg, 72%) as a white solid: $_1$H NMR (400 MHz, DMSO-$d_6$, 80° C.) d 0.73 (6H, d, J=6.8), 1.88 (1H, se, J=6.6), 2.70–2.81 (4H, m), 3.36 (1H, s), 4.09 (1H, dd, J=8.6, 6.4), 4.28–4.42 (3H, m), 4.95 (2H, s), 7.04–7.08 (2H, m), 7.12–7.32 (15H, m), 7.40–7.43 (1H, m); _C NMR (100 MHz, DMSO-$d_6$, 80° C.) d 17.3, 18.7, 29.8, 37.0, 37.9, 50.5, 55.7, 57.7, 65.0, 72.3, 125.1, 125.6, 126.8, 127.1, 127.3, 127.5, 127.7, 128.5, 128.6, 137.6, 137.9, 138.3, 155.4, 169.8, 170.6; HRMS (FAB+), calcd for MCs+ $C_{62}H_{72}N_6O_{10}Cs$ m/e 1193.4364, found m/e 1193.4323.

Biological Assays.

Kinetic determinations for both HIV PR and FIV PRs were performed at 37° C. at pH 5.25 in duplicate using F-2000 fluorescence spectrophotometer (Hitachi).

For HIV PR, the $K_M$ and $V_{max}$ values for the fluorogenic peptide substrate 2-aminobenzoyl (Abz)-Thr-Ile-Nle-Phe-(p-$NO_2$)-Gln-Arg-$NH_2$ (SEQ ID NO: 3) Toth et al Int. J. Peptide Res. 36, 544–550 were determined by measuring the initial rate of hydrolysis at different substrate concentrations (5.0, 7.5, 10, 20, 35, 50, 100, and 200 $\mu$M) by monitoring the change in fluorescence at an excitation wavelength of 325 nm and an emission wavelength of 420 nm, and fitting the obtained data to the Michaelis-Menten equation using the Grafit program (version 3.0, Erithacus Software Ltd., UK). Assays were run in 0.1 M MES buffer, containing 5% (v/v) glycerol, and 5% (v/v) DMSO (200 $\mu$l final volume). The enzyme concentration (30 $\mu$g/ml) which gave ideal progress curve was used for assays, but the dimeric active HIV PR concentration was not accurately determined. The $K_i$ for each inhibitor of HIV PR was determined by obtaining the progress curve with the inhibitor (2.0–9.0 nM) at different substrate concentrations (7.5, 10, 20, 35, and 50 mM), under the same reaction conditions as above. The curve fit the data was determined, and the subsequent $K_i$ was derived using the Grafit program.

For FIV PRs, the kinetic data were determined under the similar reaction conditions as for HIV PR. The $K_M$ and $V_{max}$ for the fluorogenic substrate Arg-Ala-Leu-Thr-Lys(Abz)-Val-Gln~nPhe-Val-Gln-Ser-Lys-Gly-Arg (SEQ ID NO: 5) were determined by monitoring the change in fluorescence at an excitation filter of 325 nm and an emission filter of 410 nm with the Grafit program under the following reaction conditions: substrate concentration (6.0, 10, 20, 35, 50, 100, and 200 $\mu$M), 0.1 M $NaH_2PO_4$ buffer containing 0.1 M Na citrate, 0.2 M NaCl, 1.0 mM DTT, 5% (v/v) glycerol, 5% (v/v) DMSO and 7.5 $\mu$g/ml (FIV(3×) and FIV(V59I)) or 2.5 $\mu$g/ml (FIV(Q99V)) of the enzyme. The $K_i$ for each inhibitor of FIV PRs was also determined by obtaining the progress curve with the inhibitor (50 nM–20 $\mu$M) at different substrate concentrations (10, 20, 35, and 50 $\mu$M).

Protease Constructs

Autoproteolysis-resistant Flv PR.

FIV(3×) was constructed as described Laco et al, J. Virol. 71, 5505–5511 and contains the G5I, N55T, and C84K codon mutations which block three primary autoproteolysis sites in the FIV PR. All clones were sequenced to confirm the modifications made to the FIV PR ORF. Kinetic analyses revealed no significant change in $K_M$ or $k_{cat}$ values between the autoproteolysis-resistant 3×PR and wild type FIV PR.

Mutant FIV PRs

Mutant FIV PRs were prepared that contained substitutions of HIV residues noted to be associated with drug resistance in HIV (16) at equivalent sites in the three dimensional structure.

(FIV(Q99V).

The feline immunodeficiency virus 34TF10 infectious molecular clone (FIV-34TF10) was used as the template in a polymerase chain reaction (PCR) using a negative strand primer (5'ATCTCTCCCCAATAATGGTACTATTAATGAGTT ATCTTCT AAGAC3' (SEQ ID NO: 6); complementary to nt's 2252–2297) which mutated the FIV PR Gln 99 codon to Val and the positive strand primer (5'ACTATTGGACATATGGCATATAATAAAGTAGG TACTACTAC3' (SEQ ID NO: 7); nt's 1964–2005) which, when incorporated into the PCR product, added an initiation Met and Ala codon to the determined 5' Tyr codon of the FIV/PR open reading frame (ORF; 19) as well as a 5' Nde I restriction site. The ~300 bp PCR product was purified and used in a second PCR with the same template and with a negative strand primer (5'ATCAGAAAGCTTTTACATTACTAACCTGATATT AAATTT3' (SEQ ID NO: 8); complementary to nt's 2306–2345) which added a stop codon after the determined C-terminal Met codon of the PR ORF in addition to a 3' Hind III restriction site, to facilitate cloning. The resulting PCR product was digested with Nde I and Hind III and ligated into pT7-7 ([35]), which had been digested with Nde I and Hind III, to give FIV(Q99V).

FIV(V591).

FIV-34TF10 was the template in a PCR reaction with the positive strand primer (5'GGAAGGCAAAATATGATTGGAATTGGAGGAG GAAAGAGAGGAACA3' (SEQ ID NO: 9); nt's 2135–2178) which mutates the FIV PR Val codon 59 to Ile, and the second negative strand primer used for FIV(Q99V). The ~200 bp PCR product was purified and used in a second PCR with the same template and the positive strand primer used for FIV(Q99V). The resulting PCR product was digested with Nde I and Hind III and ligated into pT7-7, which had been digested with Nde I and Hind III, to give FIV(V59I).

FXV Protease Expression and Purification.

All PR expression constructs were transformed into the *E. coli* cell line BL21(DE3) which contains the T7 polymerase gene under control of the Lac promoter. Cultures were induced at OD600=0.5 with 1 mM IPTG for 5 hrs with the PR inclusion bodies isolated and then solubilized in 8 M Urea, 10 mM Tris, pH 8.0, 5 mM EDTA. The PRs were subsequently purified and renatured as described Laco et al. J. Virol. 71, 5505–5511, and either stored at −70° C., or brought to 50% glycerol and stored at −20° C.

HIV PR Expression and Purification.

A recombinant plasmid bearing a portion of the Pol gene of the BH10 clone of HIV was used for amplification of sequence encoding PR. The 5' primer was constructed so as to insert an initiator methionine as part of the coding sequence for an Nde1 site, eight amino acids prior to the beginning of PR. This primer also encoded a nucleotide change to mutate Gln 7 to Lys, in order to block a major site of autoproteolysis Rose et al. J. Biol Chem 268, 11939–11945 and thus increase stability of the enzyme. The 3' primer was designed to insert a stop codon immediately following residue 99 of PR, with a Hind III site engineered 3Õ of the stop codon, to facilitate directional cloning. The PCR product was then cut with Nde1 and Hind III and inserted into the pET 21+ vector (Novagen) for protein expression.

The recombinant plasmid was transformed into the BL21.DE3, p lys S strain of *E. coli*. Inclusion bodies were prepared and solubilized essentially as described for preparation of FIV PR (24). The washed inclusion body pellet was then solubilized in 200 ml 20 mM Tris-HCl, pH 8, 1 mM DTT, 5 mM EDTA, 8 M urea with stirring at 4° C. for 1 hr. Insoluble material was removed by centrifugation at 8,000×g for 30 min. The supernatant from this centrifugation was treated batch-wise by the addition of 20 gm DE 52 anion exchange resin and the mixture was stirred at 4° C. for 1 hr. After centrifugation, PR was found in the supernatant. The resin was washed once with 50 ml resuspension buffer (above) and the wash and supernatant fractions were combined.

The supernatant/wash fraction was then passed over Resource Q anion exchange resin equilibrated in resuspension buffer, using a Pharmacia FPLC apparatus. The fraction which failed to bind to the column was concentrated using 5K cutoff UltraFree centrifugal concentrators (Millipore). The retentate was then dialyzed overnight against deionized water, which caused precipitation of PR. The pellet was recovered by centrifugation at 3,000×g for 20 min, then resuspended in 20 mM sodium acetate, pH 5.3, 1 mM DTT, 5 M GuHCl, to a concentration of 1 mg/ml (determined by Lowry assay of the pellet suspended in a known volume of water prior to final pelleting and solubilization in sodium acetate, DTT, GuHCl buffer). MALDI analysis indicated a mass of 10,792, which is within 1 mass unit of the predicted mass for the properly processed PR. Activity was monitored using a flourogenic substrate, as detailed above. Aliquots were stored at −70° C. for subsequent use.

Ex vivo Inhibitor analyses against FXV.

The lymphocytic cell line 104-C1 (provided by C. Grant) was used as the target for infection. Cells were cultured in RPMI-1640 media supplemented with 10% FBS, 200 μM L-Glutamine, 1×MEM-Vitamins, 100 μM Sodium Pyruvate, 1×Non-Essential Amino Acids, $5.5\times10_{-5}$M b-ME, 50 μg/ml Gentamicin, 50 U/ml human recombinant Interleukin-2 (provided by Hoffmann-LaRoche) and 7.5 μg/ml Concanavalin-A. For inhibitor assessment, $5\times10_6$ cells were infected with FIV-PPR ($4\times10_5$ RT units) in 1 mL culture for 2 hr at 37° C. No virus and virus only controls were incubated in a similar manner. The cells were then washed with Hanks-buffered saline solution (HBSS) and resuspended in 10 ml of complete medium. The compound 1200 (10 mg/mL in DMSO) was then added to final concentrations of 0.1, 0.5, 1, and 5 μg/ml in duplicate. The cells were then incubated at 37° C. The culture supernatants were monitored for the presence of pelletable reverse transcriptase activity at weekly intervals, as follows. Cell-free culture supernatants (4 ml) were centrifuged at 60K for 30 min and the pellets were resuspended in 100 μl of lysis buffer containing 40 mM TrisHCl (pH 8.1), 360 mM NaCl, 20 mM DTT and 0.2% NP40. Twenty five μl of lysate was added to 25 μl of a mixture containing polyrA-pdT (Pharmacia, Piscataway, N.J.), MgCl2, and 3H-labeled deoxythymidine 5'-triphosphate (DuPont NEN, Boston, Mass.), and incubated for 1 hr at 37° C. The mixture was spotted on DE81 paper, air-dried, fixed in 0.1 M sodium pyrophosphate, washed three times in 0.3 M ammonium formate, and an additional time in 95% ethanol. The paper was then dried and counted on a scintillation counter.

Cells were split 1:5 after the second, third, and fourth time points and fresh inhibitor was added at the appropriate concentration at each of these intervals. The data were expressed as values +/−standard deviation of the mean. (FIG. 2A)

Ex Vivo inhibitor analyses against HIV.

WEAU-1.6, a kind gift of George Shaw, University of Alabama ([18]), a CXCR4 utilizing isolate, was used for all studies. 2×105 MT-2 cells in 0.1 ml were infected for 4 hr, at 37° C., using WEAU-1.6 at 25 TCID50. Before establishing cultures for inhibitor assessment infected cells were washed 3 times with complete medium (CM), which was RPMI-1640 supplemented with 10% FBS, 100 mM sodium pyruvate, 200 mM L-glutamine, and 50 mg/ml of gentamicin sulfate, to remove any unbound virus. For inhibitor assessment cultures were established in duplicate or triplicate using 5×104 infected cells and 1×105 uninfected cells in a total volume of 1.5 mls in Costar 6 well-plates. Once cultures were established they were split 1:4 every 3 days, and given fresh CM. Compound 12 (from a 10 mg/ml stock in DMSO) was added at 1 or 5 mg/ml at initiation of the culture and after each split. For testiing of the antiviral efficacy of compound 1200 in MT-2 were assessed every day using a Olympus (model) inverted microscope equipped with phase contrast objectives. When MT-2 cells are infected with WEAU-1.6 they form syncytia and die with in 24 hours, events easily discernible visually. A total of 200 cells were counted in each well, and when syncytia were noted, cells were removed and tested for viability by using trypan-blue. Results are expressed as the average of viable cells.

Ex Vivo inhibitor analyses against SIV.

Stocks of SIVmac251 (provided by R. Desrosiers) were prepared in 174×CEM cells (provided by the NIH AIDS Research and Reference Program) grown in 88% RPMI medium containing 20 mM HEPES<12% heat-inactivated fetal calf serum. A 24 hr supernatant was collected at day 14 post infection and aliquoted and stored at −80° C. for subsequent experiments.

Cells were acutely infected with approximately 400 $TCID_{50}$ units of SIVmac251 for 90 min at 37° C. The cells were collected by centrifugation, washed twice with medium to remove free virus, then plated in 0.45 ml medium in 48-well tissue culture plates, at $10_5$ cells per well. Compound 1200, prepared as a 10 mg/ml stock in DMSO, was then added to final concentrations of 10, 1.0, 0.1, and 0.001 μg/ml final concentrations, in triplicate cultures. Triplicate control cultures received medium only. Uninfected cells were also cultured with the above concentrations of Compound 1200, with no effects noted. Wells were observed for the presence of syncytia at 72 and 96 hr post infection, and supernatants collected at 96 hr were assayed for relative amounts of p27 antigen, using a quantitative ELISA assay (Coulter).

What is claimed is:

1. A stereochemically pure protease inhibitor represented by the following structure:

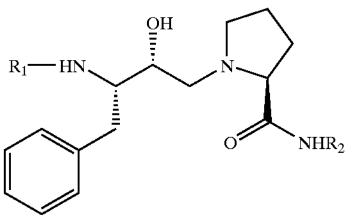

wherein $R_1$ is a radical selected from the group consisting of carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine-, carbobenzyloxy-alanine-asparagine- and carbobenzyloxy-valine-valine-; and $R_2$ is a radical selected from the group consisting of —H and -(t-Butyl).

2. A protease inhibitor represented by the following structure:

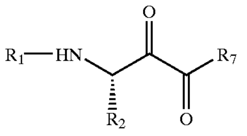

wherein $R_1$ is selected from the group consisting of carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-alanine-asparagine-, carbobenzyloxy-threonine-valine- and carbobenzyloxy-valine-valine-;

$R_2$ is selected from the group consisting of —$CH_2$-Phenyl, and —$CH_2$—$CH(CH_3)_2$;

$R_7$ is a radical represented by the formula:

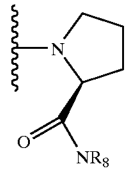

wherein $R_8$ is a radical selected from the group consisting of —$(H)_2$, and —H(t-Butyl).

3. A protease inhibitor according to claim 2 represented by the following structure:

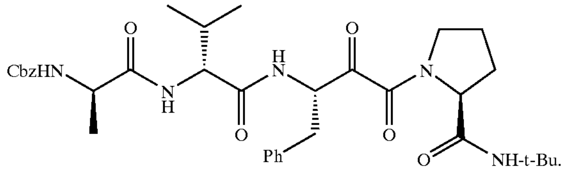

4. A protease inhibitor represented by the following structure:

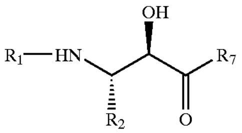

wherein $R_1$ is selected from the group consisting of carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-alanine-asparagine-, carbobenzyloxy-threonine-valine- and carbobenzyloxy-valine-valine-;

$R_2$ is selected from the group consisting of —$CH_2$-Phenyl, and —$CH_2$—$CH(CH_3)_2$;

$R_7$ is a radical represented by the formula:

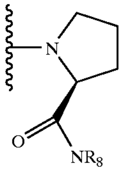

wherein $R_8$ is a radical selected from the group consisting of —$(H)_2$, and —H(t-Butyl).

5. A protease inhibitor according to claim 4 represented by the following structure:

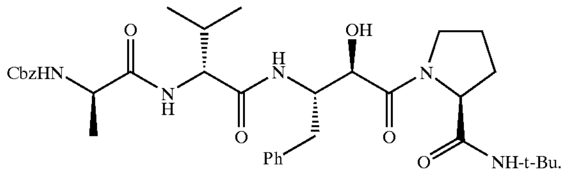

6. A stereochemically pure protease inhibitor represented by the following structure:

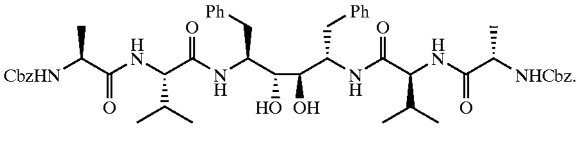

7. A protease inhibitor represented by the following structure:

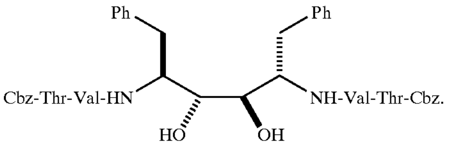

8. A protease inhibitor represented by the following structure:

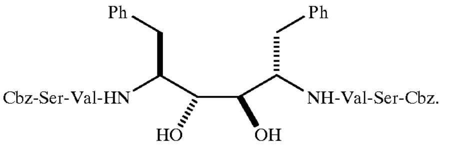

9. A stereochemically pure protease inhibitor represented by the following structure:

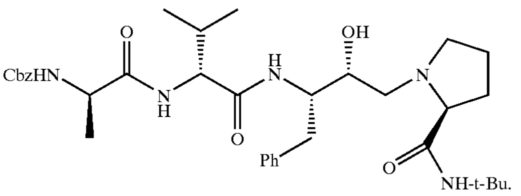

10. A protease inhibitor represented by the following structure:

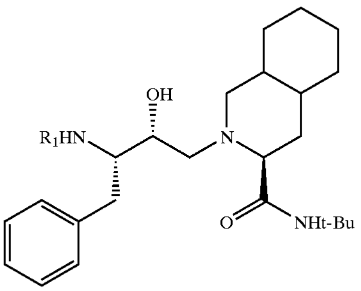

wherein $R_1$ is a radical selected from the group consisting of carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine-, carbobenzyloxy-valine-valine- and carbobenzyloxy-alanine-asparagine-.

11. A protease inhibitor according to claim 10 represented by the following structure:

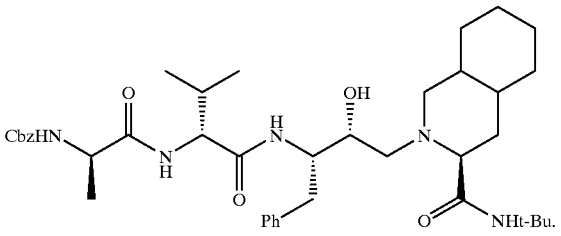

12. A protease inhibitor represented by the following structure:

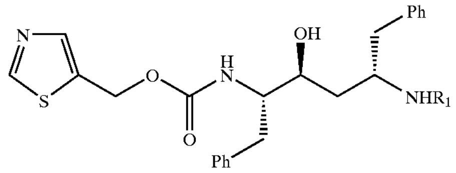

wherein $R_1$ is a radical selected from the group consisting of carbobenzyloxy-valine-, carbobenzyloxy-glycine-valine-, carbobenzyloxy-alanine-valine-, carbobenzyloxy-leucine-valine-, carbobenzyloxy-phenylalanine-valine-, carbobenzyloxy-serine-valine-, carbobenzyloxy-threonine-valine-, carbobenzyloxy-valine-valine- and carbobenzyloxy-alanine-asparagine-.

13. A protease inhibitor according to claim 12 represented by the following structure:

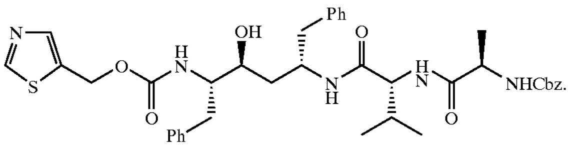

* * * * *

UNITED STATES PATENT AND TRADEMARK OFFICE

CERTIFICATE OF CORRECTION

PATENT NO. : 6,803,466 B1 Page 1 of 1
DATED : October 12, 2004
INVENTOR(S) : Taekyu Lee, Chi-Huey Wong and John H. Elder It is certified that error appears in the above-identified patent and that said Letters Patent is hereby corrected as shown below:

Column 1,
Line 5, insert:
-- This invention was made with Government support under Contract No. GM48870 by the National Institutes of Health. The Government has certain rights in the invention. --.

Signed and Sealed this

Twenty-fifth Day of October, 2005

JON W. DUDAS
*Director of the United States Patent and Trademark Office*